US006586197B1

(12) United States Patent
Adang et al.

(10) Patent No.: US 6,586,197 B1
(45) Date of Patent: Jul. 1, 2003

(54) METHODS AND MATERIALS FOR IDENTIFYING NOVEL PESTICIDE AGENTS

(75) Inventors: Michael J. Adang, Athens, GA (US); Ke Luo, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/657,931

(22) Filed: Sep. 7, 2000

Related U.S. Application Data
(60) Provisional application No. 60/153,116, filed on Sep. 7, 1999.

(51) Int. Cl.$^7$ .............................. C12Q 1/37; C12N 9/64; C12N 15/57
(52) U.S. Cl. .......................... 435/23; 435/219; 435/348; 536/23.2
(58) Field of Search .......................... 435/348, 23, 219; 536/23.2

(56) References Cited

PUBLICATIONS

Ayres, M.D., Howard, S.C., Kuzio, J., Lopez–Ferber, M. and Dossec, R.D. (1994) "The complete DNA sequence of *Autograph californica* nuclear polyhedrosis virus," *Virology* 202:586–605.

Benbacer, L., Kut, E., Besnardeau, L., Laude, H. and Delmas, B. (1997) "Interspecies aminopeptidase–N chimeras reveal species–specific receptor recognition by canine coronavirus, feline infectious peritonitis virus, and transmissible gastroenteritis virus," *J. Virol.* 71:734–737.

Chaudhri, M., Steverding, D., Kittelberger, D., Tjia, S. and Overath, P. (1994) "Expression of glycosylphosphadylinositol–anchored *Trypanosoma brucei* transferrin–binding protein complex in insect cells," *Proc. Natl. Acad. Sci. U.S.A.* 91:6443–6447.

Davies, A. and Morgan, B. P. (1993) "Expression of the glycosylphosphatidlinositol–linked complement–inhibiting protein CD59 antigen in insect cells using a baculovirus vector," *Biochemical Journal* 295:889–896.

Delmas, B., Gelfi, J., Haridon, R.L., Vogel, L.K., Sjostrom, H., Noren, O. and Laude, H. (1992) "Aminopeptidase N is a major receptor for the enteropathogenic coronavirus TGEV," *Nature* 357:417–419.

Denolf, P., Hendrickx, K., Van Damme, J., Jansens, S., Peferoen, M., Degheele, D. and Van Rie, J. (1997) "Cloning and characterization of *Manduca sexta* and *Plutella xylostella* midgut aminopeptidase N enzymes related to *Bacillus thuringiensis* toxin–binding proteins," *Eur. J. Biochem.* 248:748–761.

Ferre, J., Real, M.D., Van Rie, J., Jansens, S. and Peferoen, M. (1991) "Resistance to the *Bacillus thuringiensis* bioinsecticide in a field population of *Plutella xylostella* is due to a change in a midgut membrane receptor," *Proc. Natl. Acad. Sci. USA* 88:5119–5123.

Garczynski, S.F. and Adang, M.J. (1995) "*Bacillus thuringiensis* CryIA(c) d–endotoxin binding aminopeptidase in the *Manduca sexta* midgut has a glycosyl–phosphatidylinositol anchor," *Insect Biochem. Mol. Biol.* 25:409–415.

Garczynski, S.F., Crim, J.W. and Adang, M.J. (1991) "Identification of putative brush border membrane binding proteins specific to *Bacillus thuringiensis* delta–endotoxin by protein blot analysis," *Appl. Environ. Microbiol.* 57:2816–2820.

Gill, S., Cowles, E.A. and Francis, V. (1995) "Identification, isolation, and cloning of a *Bacillus thuringiensis* CryIAc toxin–binding protein from the midgut of the lepidopteran insect *Heliothis virescens,*" *J. Biol. Chem.* 270:27277–27282.

Hua, G., Tsukamoto, K., Rasilo, M. and Ikezawa, H. (1998) "Molecular cloning of a GPI–anchored aminopeptidase N from *Bombyx mori* midgut: a putative receptor for *Bacillus thuringiensis* CryIA toxin," *Gene* 214:177–185.

Kenny, A.J., Stephenson, S.L. and Turner, A.J. (1987) "Cell surface peptidases," In Kenny, A.J. and Turner, A.J. (eds.) *Mammalian ectoenzymes*, Elsevier, Amsterdam, pp. 169–210.

Knight, P.J.K., Crickmore, N. and Ellar, D.J. (1994) "The receptor for *Bacillus thuringiensis* CryIA(c) delta–endotoxin in the brush border membrane is aminopeptidase N," *Mol. Microbiol.* 11:429–436.

Knight, P.J.K., Knowles, B.H. and Ellar, D.J. (1995) "Molecular cloning of an insect aminopeptidase N that serves as a receptor for *Bacillus thuringiensis* CryIA(c) toxin," *J. Biol. Chem.* 270:17765–1770.

Kozak, M. (1987) "An analysis of 5'–noncoding sequences from 699 vertebrate messenger RNAs," *Nucl. Acids Res.* 15:8125–8132.

Laemmli, U.K. (1970) "Cleavage of structural proteins during the assembly of the head of bacteriophage T4," *Nature* 227:680–685.

Look, A.T., Ashmun, R.A., Shapiro, L.H. and Peiper, S.C. (1989) "Human myeloid plasma membrane glycoprotein CD13 (gp150) is identical to aminopeptidase N," *J. Clin. Invest.* 83:1299–1307.

(List continued on next page.)

Primary Examiner—Charles L. Patterson, Jr.
(74) Attorney, Agent, or Firm—Saliwanchik, Lloyd & Saliwanchik

(57) ABSTRACT

Materials and methods for identifying novel pesticide agents are disclosed herein. Specifically exemplified is a full length aminopeptidase N isolated from *Manduca sexta*, insect cells expressing APN, and methods of screening pesticide agents using the same. Also disclosed are methods of identifying novel APN inhibitors.

9 Claims, 17 Drawing Sheets

OTHER PUBLICATIONS

Lu, Y. and Adang, M.J. (1996) "Conversion of *Bacillus thuringiensis* CryIAc–binding aminopeptidase to a soluble form by endogenous phosphatidylinositol phospholipase C," *Insect Biochem. Molec. Biol.* 26:33–40.

Luo, K., Lu, Y.J. and Adang, M.J. (1996) "A 106 kDa form of aminopeptidase is a receptor for *Bacillus thuringiensis* CryIC delta–endotoxin in the brush border membrane of *Manduca sexta*," *Insect Biochem. Mol. Biol.* 26:783–791.

Luo, K., Sangadala, S., Masson, L., Mazza, A., Brousseau, R. and Adang, M.J. (1997a) "The *Heliothis virescens* 170–kDa aminopeptidase functions as 'Receptor A' by mediating specific *Bacillus thuringiensis* Cry1A d–endotoxin binding and pore formation," *Insect Biochem. Mol. Biol.* 27(8/9):735–743.

Luo, K., Tabashnik, B.E. and Adang, M.J. (1997b) "Binding of *Bacillus thuringiensis* Cry1Ac toxin to aminopeptidase in susceptible and resistant diamondback moths (*Plutella xylostella*)," *Appl. Environ. Microbiol.* 63:1024–1027.

Luo, K., McLachlin, J.R., Brown, M.R., Adang, M.J. (1999) "Expression of a Glycosylphosphatidylinositol–Linked *Manduca sexta* Aminopeptidase N in Insect Cells," *Protein Expression and Purification* 17:113–122.

Masson, L., Lu, Y., Mazza, Brosseau, R. and Adang, M.J. (1995) "The CryIA(c) receptor purified from *Manduca sexta* displays multiple specificities," *J. Biol. Chem.* 270:20309–20315.

McConville, M. J. and Ferguson, M. A. J. (1993) "The structure, biosynthesis and function of glycosylated phosphatidylinositols in the parasitic protozoa and higher eukaryotes," *Biochemical Journal* 294:305–324.

McLaughlin, S. and Aderem, A. (1995) "The myristoyl–electrostatic switch: a modulator of reversible protein–membrane interactions," *TIBS* 20:272–276.

Morris, T.D. and Miller, L.K. (1992) "Promoter influence on baculovirus–mediated gene expression in permissive and non–permissive insect cell lines," *J. Virol.* 66:7397–7405.

Plakidou–dymock, S., Tanner, M.J. and McGivan, J.D. (1993) "A role for aminopeptidase N in $Na^+$–dependent amino acid transport in bovine renal brush–border membranes," *Biochem. J.* 290:59–65.

Richardson, M.A., Smith, D.R.J., Kemp, D.H. and Tellam, R.L. (1993) "Native and baculovirus–expressed forms of the immunoprotective protein BM86 from boophilus microplus are anchored to the cell membrane by a glycosylphosphatidyl inositol linkage," *Insect Mol. Biol.* 1:139–147.

Sangadala, S., Walters, F., English, L.H. and Adang, M.J. (1994) "A mixture of *Manduca sexta* aminopeptidase and alkaline phosphatase enhances *Bacillus thuringiensis* insecticidal CryIA(c) toxin binding and $^{86}Rb^+$–$K^+$ leakage in Vitro," *J. Biol. Chem.* 269:10088–10092.

Schwartz, J.–L., Lu, Y.J., Soehnlein, P., Brosseau, R., Masson, L., Laprade, R. and Adang, M.J. (1997) "Ion channels formed in planar lipid bilayers by *Bacillus thuringiensis* toxins in the presence of *Manduca sexta* midgut receptors," *FEBS Lett.* 412:270–276.

Takasaki, S., Erickson, R.H., Kim, Y.S., Kochibe, N. and Kobata, A. (1991) "N–linked neutral sugar chains of aminopeptidase N purified from rat small intestinal brush–border membrane," *Biochem.* 30:9102–9110.

Tomita, M., Obara, H., Takesue, Y., Tamura, H.–O., Miyajima, s., Taguchi, R. and Ikezawa, H. (1994) "Purification of glycosylphosphatidylinositol–anchoring aminopeptidase N from the plasma membrane of larval midgut epithelial cells of the silkworm, *Bombyx mori*," *Int. J. Biochem.* 26:977–986.

Towbin, H., Staehelin, T. and Gordon, J. (1979) "Electrophoretic transfer of proteins from polyacrylamide gels to nitrocellulose sheets: procedure and some applications," *Proc. Natl. Acad. Sci. USA* 76:4350–4354.

Tresnan, N.B., Levis, R. and Holmes, K.V. (1996) "Feline aminopeptidase N serve as a receptor for feline, canine, porcine, and human coronaviruses in serogroup I," *J. Virol.* 70:8669–8674.

Valaitis, A., Lee, M.K., Rajamohan, F. and Dean, D.H. (1995) "Brush border membrane aminopeptidase–N in the midgut of the gypsy moth serves as the receptor for the CryIA(c) d–endotoxin of *Bacillus thuringiensis*," *Insect Biochem. Molec. Biol.* 25:1143–1151.

Vaughn, J.L., Goodwin, R.H., Tompkins, G.L. and McCawley, P. (1977) "The establishment of two insect cell lines from the insect *Spodoptera frugiperda* (Lepidoptera:Noctuidae)," *In Vitro Cell. Dev. Biol.* 13:213–217.

Wolfersberger, M.G., Luthy, P., Maurer, A., Parenti, P., Sacchi, V.F., Giordana, B. and Hanozet, G.M. (1987) "Preparation and partial characterization of amino acid transporting brush border membrane vesicles from the larval midgut of the cabbage butterfly (*Pieris brassicae*)," *Comp. Biochem. Physiol.* 86A:301–308.

Yaoi, K., Kadotani, T., Kuwana, H., Shinkawa, A., Takahashi, T., Iwahana, H. and Sato, M. (1997) "Aminopeptidase N from *Bombyx mori* as a candidate for the receptor of *Bacillus thuringiensis* Cry1Aa toxin," *Eur. J. Biochem.* 246:652–657.

Yeager, C.L., Ashmun, R.A., Williams, R.K., Cardellichio, C.B., Shapiro, L.H., Look, A.T. and Holmes, K.V. (1992) "Human aminopeptidase N is a receptor for human coronavirus 229E," *Nature* 357:420–422.

Fujii, H., Nakajima, M., Saiki, I., Yoneda, J., Azuma, I., and Tsuruo, T. (1995) "Human melanoma invasion and metastasis enhancement by high expression of aminopeptidase N/CD13," *Clin. Exp. Metast.* 13:337–344.

Kennard, M.L., Shimizu, K.Y., Gabathuler, R., Rothenberger, S., Theilmann, D. and Jefferies, W.A. (1997) "Expression of cell surface GPI–anchored human p97 in baculovirus–infected insect cells," *Biotech. Bioeng.* 55:41–53.

Kolb, A.F., Maile, J., Heister, A. and Siddell, S.G. (1996) "Characterization of functional domains in the human coronavirus HCV 229E receptor," *J. Gen. Virol.* 77:2515–2521.

```
ATGGTGAATCTCGGGTTTACCATTTTCTTGGGGGTCGCCCTTCTCCAGGGCGTTCTTACT
-+---------+---------+---------+---------+---------+--------   78
MetValAsnLeuGlyPheThrIlePheLeuGlyValAlaLeuLeuGlnGlyValLeuThr

TTGAGCCCCATACCCGTCCCAGAAGAAGAATGGGCCGAATTCTCCAGAATGCTGCGGGAC
-+---------+---------+---------+---------+---------+--------   138
LeuSerProIleProValProGluGluGluTrpAlaGluPheSerArgMetLeuArgAsp

CCGAGCTACCGCCTGCCTACTACCACCCGGCCAAGACATTACGCTGTGACCCTGACTCCA
-+---------+---------+---------+---------+---------+--------   198
ProSerTyrArgLeuProThrThrThrArgProArgHisTyrAlaValThrLeuThrPro

TACTTTGACGTGGTACCTGCTGGTGTCAGCAGCCTTACCACCTTCAGCTTTGACGGCGAG
-+---------+---------+---------+---------+---------+--------   258
TyrPheAspValValProAlaGlyValSerSerLeuThrThrPheSerPheAspGlyGlu

GTCACCATCTACATATCGCCCACTCAAGCTAATGTTAATGAGATCGTCCTCCACTGCAAT
-+---------+---------+---------+---------+---------+--------   318
ValThrIleTyrIleSerProThrGlnAlaAsnValAsnGluIleValLeuHisCysAsn

GACTTGACGATACAGAGTCTGAGGGTAACATATGTTAGTGGTAATAGTGAGGTGGATATC
-+---------+---------+---------+---------+---------+--------   378
AspLeuThrIleGlnSerLeuArgValThrTyrValSerGlyAsnSerGluValAspIle

ACGGCAACTGGACAAACTTTTACGTGTGAGATGCCCTACAGTTTTCTCAGAATAAGGACC
-+---------+---------+---------+---------+---------+--------   438
ThrAlaThrGlyGlnThrPheThrCysGluMetProTyrSerPheLeuArgIleArgThr

TCTACGCCTCTAGTGATGAACCAAGAGTATATTATCAGGAGTACCTTTAGAGGCAACTTG
-+---------+---------+---------+---------+---------+--------   498
SerThrProLeuValMetAsnGlnGluTyrIleIleArgSerThrPheArgGlyAsnLeu

CAGACTAACATGAGAGGGTTCTACAGAAGTTGGTACGTCGATAGAACCGGAAAGAGATGG
-+---------+---------+---------+---------+---------+--------   558
GlnThrAsnMetArgGlyPheTyrArgSerTrpTyrValAspArgThrGlyLysArgTrp

ATGGCTACCACTCAACTTCAACCCGGACATGCGCGTCAAGCGTTCCCTTGCTACGATGAG
-+---------+---------+---------+---------+---------+--------   618
MetAlaThrThrGlnLeuGlnProGlyHisAlaArgGlnAlaPheProCysTyrAspGlu

CCTGGTTTCAAGGCCACCTTCGACATTACTATGAACAGAGAAGCCGACTTTAGCCCGACC
-+---------+---------+---------+---------+---------+--------   678
ProGlyPheLysAlaThrPheAspIleThrMetAsnArgGluAlaAspPheSerProThr

ATATCTAATATGCCTATTAGGGCCACTACCACGCTCACGAATGGACGTATTTCCGAAACA
```

Figure 2A

```
                                                                      738
IleSerAsnMetProIleArgAlaThrThrThrLeuThrAsnGlyArgIleSerGluThr

TTTTTCACCACTCCCTTGACATCCACCTATCTCCTTGCCTTCATAGTCTCTCACTATCAG
                                                                      798
PhePheThrThrProLeuThrSerThrTyrLeuLeuAlaPheIleValSerHisTyrGln

GTCATTTCTAACAACAACAATGCAGCACGCCCTTTTAGAATCTATGCACGTAATAATGTA
                                                                      858
ValIleSerAsnAsnAsnAsnAlaAlaArgProPheArgIleTyrAlaArgAsnAsnVal

GGGAGCCAGGGTGACTGGTCTCTTGAAATGGGTGAGAAACTGCTATTAGCTATGGAGAAT
                                                                      918
GlySerGlnGlyAspTrpSerLeuGluMetGlyGluLysLeuLeuLeuAlaMetGluAsn

TATACTGCAATACCTTATTACACGATGGCACAAAACATTGATATGAAACAAGCCGCCATT
                                                                      978
TyrThrAlaIleProTyrTyrThrMetAlaGlnAsnIleAspMetLysGlnAlaAlaIle

CCCGACTTCTCTGCTGGTGCTATGGAAAACTGGGGTCTCTTGACATACAGGGAAGCCCTC
                                                                     1038
ProAspPheSerAlaGlyAlaMetGluAsnTrpGlyLeuLeuThrTyrArgGluAlaLeu

ATCTTATACGACCCCCTCAATTCGAACCATCACTACCGTCAGCGCGTAGCGAACATTGTC
                                                                     1098
IleLeuTyrAspProLeuAsnSerAsnHisHisTyrArgGlnArgValAlaAsnIleVal

TCCCACGAGATCGCTCACATGTGGTTCGGTAACCTTGTCACATGCGCATGGTGGGATAAC
                                                                     1158
SerHisGluIleAlaHisMetTrpPheGlyAsnLeuValThrCysAlaTrpTrpAspAsn

CTTTGGCTGAACGAAGGTTTTGCGCGGTTCTACCAATACTACCTTACTGCAACGGTCGAC
                                                                     1218
LeuTrpLeuAsnGluGlyPheAlaArgPheTyrGlnTyrTyrLeuThrAlaThrValAsp

CCAGAGCTCGGTTATGAAATTCGTTTCATCCCAGAGCAGCTTCAAGTGGCGATGTTCTCT
                                                                     1278
ProGluLeuGlyTyrGluIleArgPheIleProGluGlnLeuGlnValAlaMetPheSer

GACTCCGTAGACAGCGCCCACGCTCTTACTGACACCAGTGTTAATGATCCTGTTGCTGTC
                                                                     1338
AspSerValAspSerAlaHisAlaLeuThrAspThrSerValAsnAspProValAlaVal

AGCGCTCACTTCTCAACAATCACTTACGCCAGGGGAGCCGCCATCCTCAGAATGACACAG
                                                                     1398
SerAlaHisPheSerThrIleThrTyrAlaArgGlyAlaAlaIleLeuArgMetThrGln
```

Figure 2B

```
CATTTGTTGAGCTATGACACCTTCGTCAAAGGTCTTAGGCAGTATCTGCGTGCTCGACAA
-+---------+---------+---------+---------+---------+--------    1458
HisLeuLeuSerTyrAspThrPheValLysGlyLeuArgGlnTyrLeuArgAlaArgGln

TTTGACGTCGCCGAACCCTACCACCTGTTCTCCGCTTTGGATGCTGCGGCTGCTGAAGAC
-+---------+---------+---------+---------+---------+--------    1518
PheAspValAlaGluProTyrHisLeuPheSerAlaLeuAspAlaAlaAlaAlaGluAsp

AATGCTCTCGCTGCCTACACAGGCATCACTATTGACGCTTACTTCAGGACTTGGTCAGAG
-+---------+---------+---------+---------+---------+--------    1578
AsnAlaLeuAlaAlaTyrThrGlyIleThrIleAspAlaTyrPheArgThrTrpSerGlu

AAGGCGGGACATCCCCTTCTCTCAGTTACTGTTGATCATGAAACCGGCCGTATGACTCTC
-+---------+---------+---------+---------+---------+--------    1638
LysAlaGlyHisProLeuLeuSerValThrValAspHisGluThrGlyArgMetThrLeu

GTTCAGGCAAGATGGGAGCGCAATACCGGTGTGTCTCGATTCCCGGGCTTATGGCATATC
-+---------+---------+---------+---------+---------+--------    1698
ValGlnAlaArgTrpGluArgAsnThrGlyValSerArgPheProGlyLeuTrpHisIle

CCTATCACATGGACAAGGGCTGGAGCCCCAGACTTCGAAAACCTGAAGCCCTCGCAAGTT
-+---------+---------+---------+---------+---------+--------    1758
ProIleThrTrpThrArgAlaGlyAlaProAspPheGluAsnLeuLysProSerGlnVal

ATGACTGGACAGTCTTTAGTCATTGACCGTGGTACCAGAGGACAAGAGTGGGTCATCTTC
-+---------+---------+---------+---------+---------+--------    1818
MetThrGlyGlnSerLeuValIleAspArgGlyThrArgGlyGlnGluTrpValIlePhe

AACAAGCAAGTATCAGGTTTCTACCGTGTCAACTACGATAATACCACCTGGGGTCTCATC
-+---------+---------+---------+---------+---------+--------    1878
AsnLysGlnValSerGlyPheTyrArgValAsnTyrAspAsnThrThrTrpGlyLeuIle

ACAAGGGCTCTGAGGTCTGCGAACAGGACAGTTATTCACGAATTGAGTCGCTCTCAGATA
-+---------+---------+---------+---------+---------+--------    1938
ThrArgAlaLeuArgSerAlaAsnArgThrValIleHisGluLeuSerArgSerGlnIle

GTAGACGATGTCTTCCAACTGGCTAGATCCGGCGTGATGTCATACCAACGAGCACTTAAC
-+---------+---------+---------+---------+---------+--------    1998
ValAspAspValPheGlnLeuAlaArgSerGlyValMetSerTyrGlnArgAlaLeuAsn

ATTCTGTCCTACTTGAGATTCGAAGACGCGTACGCACCGTGGTTGTCCGCCATCAGCGGG
-+---------+---------+---------+---------+---------+--------    2058
IleLeuSerTyrLeuArgPheGluAspAlaTyrAlaProTrpLeuSerAlaIleSerGly

TTCAACTGGGTCATCAGGAGATTCGCCCATGACGCCGCCAATTTACAAACTTTACAGAAC
-+---------+---------+---------+---------+---------+--------    2118
```

Figure 2C

```
PheAsnTrpValIleArgArgPheAlaHisAspAlaAlaAsnLeuGlnThrLeuGlnAsn

CAAATCATCGGACTGAGCGAAGCTGTGGTGGCTCGGCTTGGCTTCACCGAAGTATCCGGT
-+---------+---------+---------+---------+---------+--------     2178
GlnIleIleGlyLeuSerGluAlaValValAlaArgLeuGlyPheThrGluValSerGly

GGTACTTATATGACCGACCTCCAGAGGTTGCATGTAATGCAGTTTCTCTGCAATGTGGGA
-+---------+---------+---------+---------+---------+--------     2238
GlyThrTyrMetThrAspLeuGlnArgLeuHisValMetGlnPheLeuCysAsnValGly

CATCAGCAGTGCATTGACACTGGAAGACAGAACTTCTTGAACTGGAGGAACGGTAGCTTT
-+---------+---------+---------+---------+---------+--------     2298
HisGlnGlnCysIleAspThrGlyArgGlnAsnPheLeuAsnTrpArgAsnGlySerPhe

ATCCCAGCTAACATGCGTCCATGGGTGTACTGCACTGGTCTTCGTTACGGCTCTGCTGAG
-+---------+---------+---------+---------+---------+--------     2358
IleProAlaAsnMetArgProTrpValTyrCysThrGlyLeuArgTyrGlySerAlaGlu

GACTTCAATTACTTCTGGAATCGTTACATCGTAGAAGATCTGTCTAATGAAAAGGTTGTG
-+---------+---------+---------+---------+---------+--------     2418
AspPheAsnTyrPheTrpAsnArgTyrIleValGluAspLeuSerAsnGluLysValVal

ATGCTCGAAGCGGCCGGTTGCACGCGTGACCAGGCCAGCTTGGAGAAGTTCTTGAACGCT
-+---------+---------+---------+---------+---------+--------     2478
MetLeuGluAlaAlaGlyCysThrArgAspGlnAlaSerLeuGluLysPheLeuAsnAla

ATCGTTTCTGGCAATGATGACGTCAGACCACAGGATCATTCGAGTGCCCTGAGCTCAGCT
-+---------+---------+---------+---------+---------+--------     2538
IleValSerGlyAsnAspAspValArgProGlnAspHisSerSerAlaLeuSerSerAla

ATCACATCCAACGACGTCAACACCATGAGAGCGTTCGACTGGTTGACCAAGAATGTAGAT
-+---------+---------+---------+---------+---------+--------     2598
IleThrSerAsnAspValAsnThrMetArgAlaPheAspTrpLeuThrLysAsnValAsp

CAAATTACACGAACTCTTGGTAGTATCACCTCGCCGCTGAACACCATCACGAGCCGTCTC
-+---------+---------+---------+---------+---------+--------     2658
GlnIleThrArgThrLeuGlySerIleThrSerProLeuAsnThrIleThrSerArgLeu

TTGACCGAGGCACAGATGACTCAGGTACAAACTTGGCTTGACGCAAACCGTAACACCATC
-+---------+---------+---------+---------+---------+--------     2718
LeuThrGluAlaGlnMetThrGlnValGlnThrTrpLeuAspAlaAsnArgAsnThrIle

GGCGCTGCCTACAACACTGGCGTGAACGGCATCGCCACATCGAGAGCTAATCTCCAGTGG
-+---------+---------+---------+---------+---------+--------     2778
GlyAlaAlaTyrAsnThrGlyValAsnGlyIleAlaThrSerArgAlaAsnLeuGlnTrp
```

Figure 2D

```
TCGGCGAACAGAATGTCTGAGTTCCTGCGCTTCTTCGAAACTGGGTTCGTCGACGATGTT
-+---------+---------+---------+---------+---------+--------   2838
SerAlaAsnArgMetSerGluPheLeuArgPhePheGluThrGlyPheValAspAspVal

CCTAGTGAGGCGACTACTGTTGCGCCCCCTGCCGAAACTACGGTGACTCCCTCTACCTTC
-+---------+---------+---------+---------+---------+--------   2898
ProSerGluAlaThrThrValAlaProProAlaGluThrThrValThrProSerThrPhe

CCTCCGACGGAAGCACCGGCGACTACTCCAGCCCCGGGCTCAGGAAACATCGCCGCTTTG
-+---------+---------+---------+---------+---------+--------   2958
ProProThrGluAlaProAlaThrThrProAlaProGlySerGlyAsnIleAlaAlaLeu

AGCGTTGTCAGCCTCCTCGTCACACTTGCCATTAACATGGTAGCGTAA
-+---------+---------+---------+---------+------   3006
SerValValSerLeuLeuValThrLeuAlaIleAsnMetValAlaEnd
```

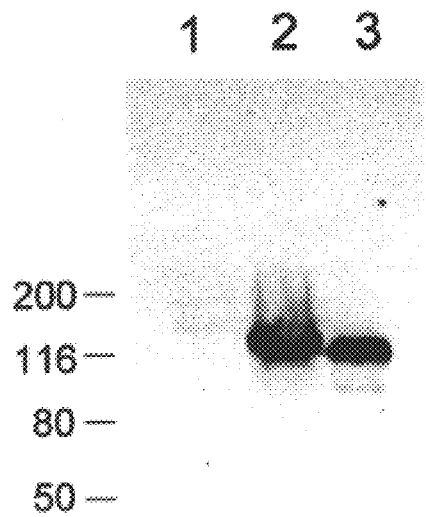
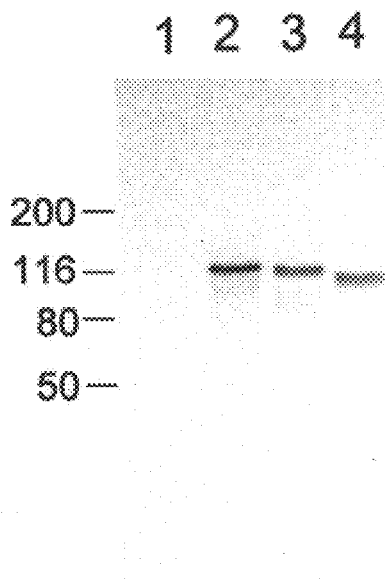
Figure 4
Figure 5
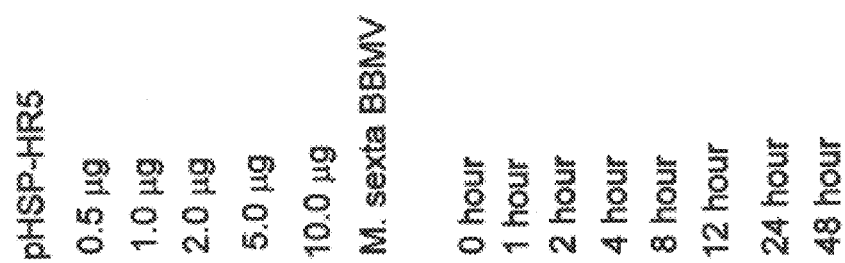
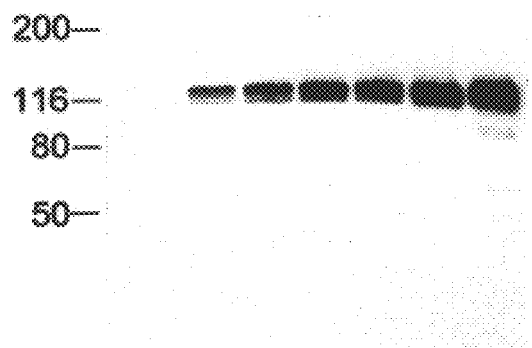
Figure 6A
Figure 6B

Figure 10A   Figure 10B
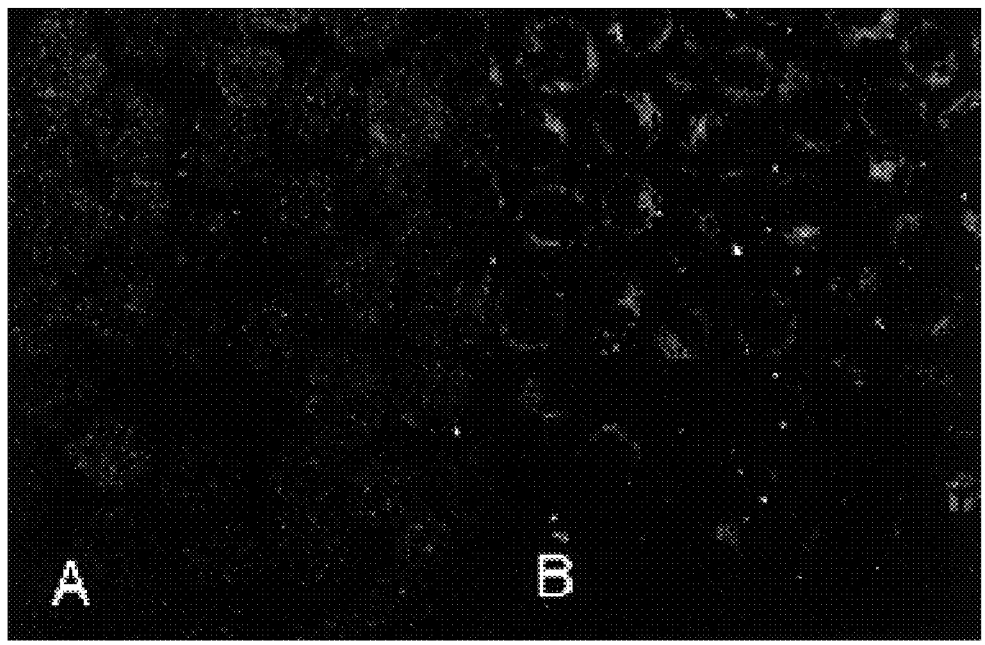
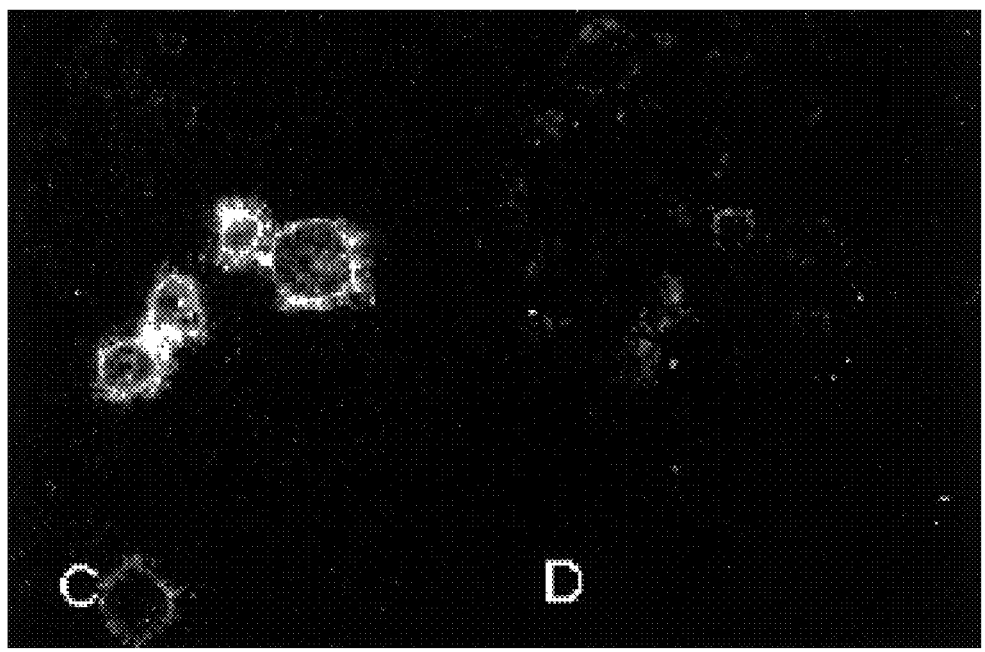
Figure 10C   Figure 10D

Figure 11A   Figure 11B
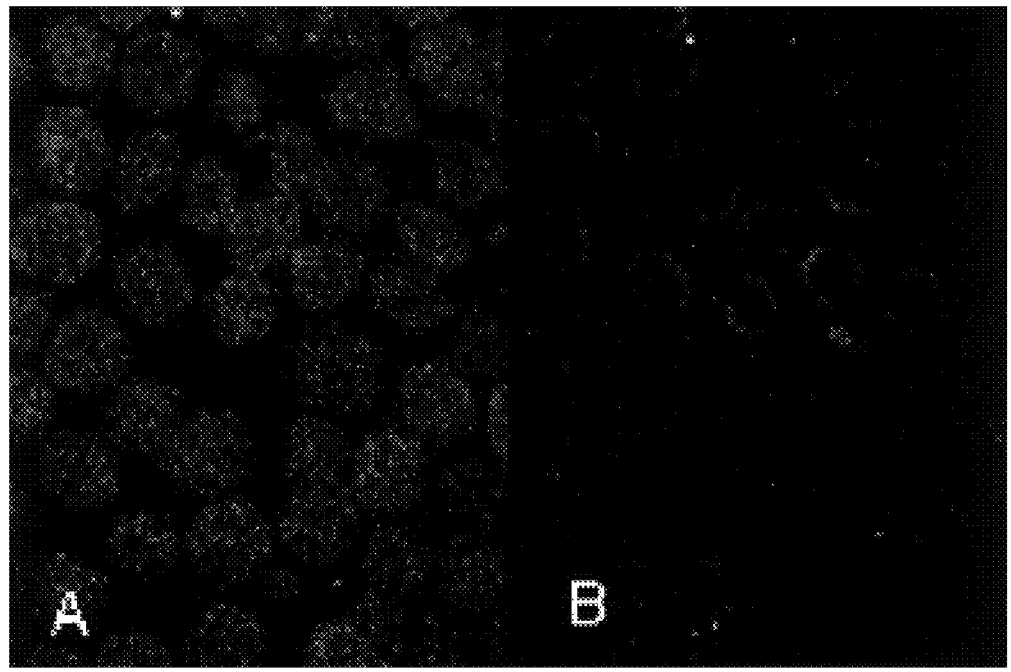
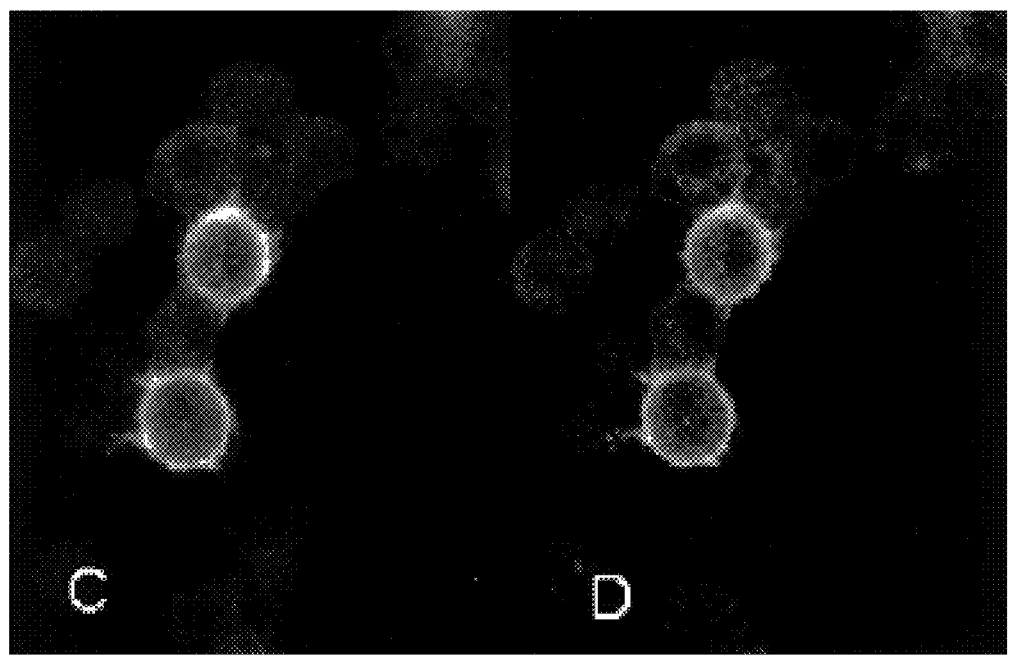
Figure 11C   Figure 11D

Figure 12A  Figure 12B
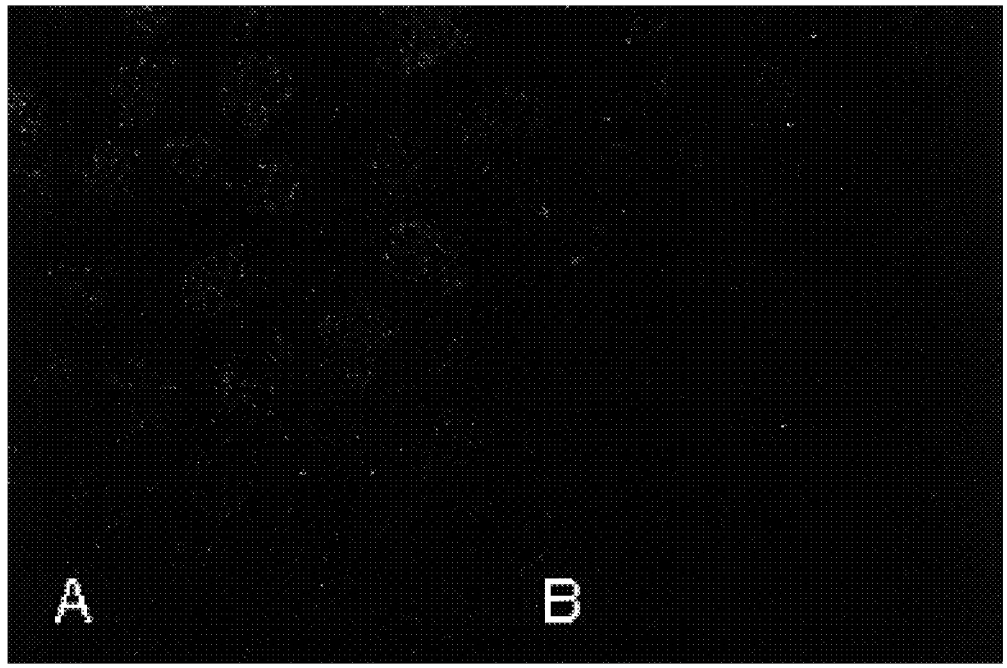
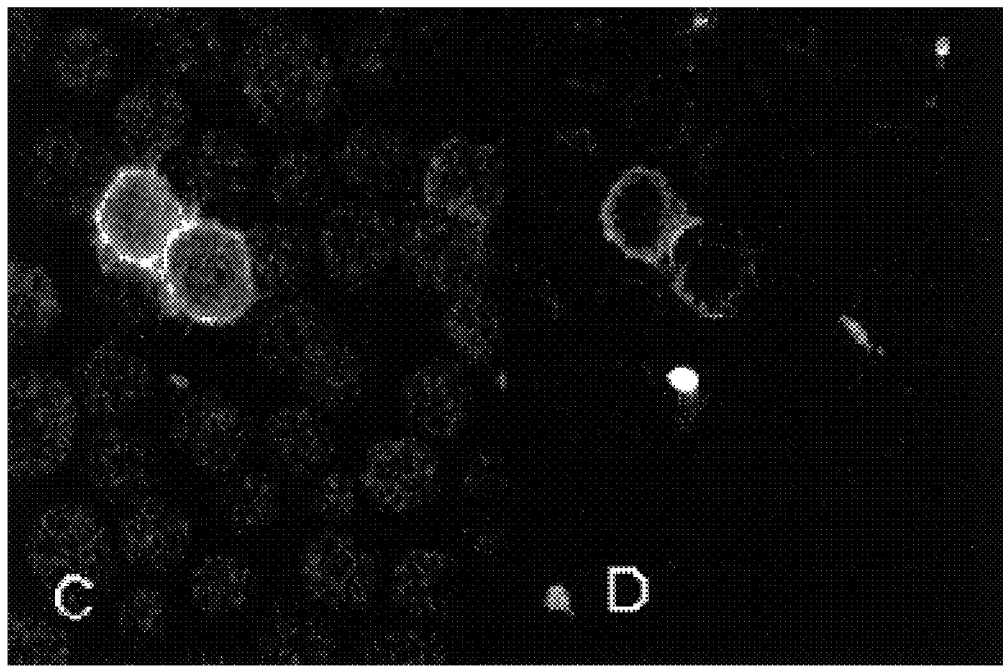
Figure 12C  Figure 12D

Figure 14

SEQUENCE LISTING

<160> NUMBER OF SEQ ID NOS: 15

<210> SEQ ID NO 1
<211> LENGTH: 995
<212> TYPE: PRT
<213> ORGANISM: Manduca sexta

<400> SEQUENCE: 1

```
Met Val Asn Leu Gly Phe Thr Ile Phe Leu Gly Val Ala Leu Leu Gln
1               5                   10                  15

Gly Val Leu Thr Leu Ser Pro Ile Pro Val Pro Glu Glu Glu Trp Ala
            20                  25                  30

Glu Phe Ser Arg Met Leu Arg Asp Pro Ser Tyr Arg Leu Pro Thr Thr
        35                  40                  45

Thr Arg Pro Arg His Tyr Ala Val Thr Leu Thr Pro Tyr Phe Asp Val
    50                  55                  60

Val Pro Ala Gly Val Ser Ser Leu Thr Thr Phe Ser Phe Asp Gly Glu
65                  70                  75                  80

Val Thr Ile Tyr Ile Ser Pro Thr Gln Ala Asn Val Asn Glu Ile Val
                85                  90                  95

Leu His Cys Asn Asp Leu Thr Ile Gln Ser Leu Arg Val Thr Tyr Val
            100                 105                 110

Ser Gly Asn Ser Glu Val Asp Ile Thr Ala Thr Gly Gln Thr Phe Thr
        115                 120                 125

Cys Glu Met Pro Tyr Ser Phe Leu Arg Ile Arg Thr Ser Thr Pro Leu
    130                 135                 140

Val Met Asn Gln Glu Tyr Ile Ile Arg Ser Thr Phe Arg Gly Asn Leu
145                 150                 155                 160

Gln Thr Asn Met Arg Gly Phe Tyr Arg Ser Trp Tyr Val Asp Arg Thr
                165                 170                 175

Gly Lys Arg Trp Met Ala Thr Thr Gln Leu Gln Pro Gly His Ala Arg
            180                 185                 190

Gln Ala Phe Pro Cys Tyr Asp Glu Pro Gly Phe Lys Ala Thr Phe Asp
        195                 200                 205

Ile Thr Met Asn Arg Glu Ala Asp Phe Ser Pro Thr Ile Ser Asn Met
    210                 215                 220

Pro Ile Arg Ala Thr Thr Thr Leu Thr Asn Gly Arg Ile Ser Glu Thr
225                 230                 235                 240

Phe Phe Thr Thr Pro Leu Thr Ser Thr Tyr Leu Leu Ala Phe Ile Val
                245                 250                 255

Ser His Tyr Gln Val Ile Ser Asn Asn Asn Ala Ala Arg Pro Phe
            260                 265                 270

Arg Ile Tyr Ala Arg Asn Asn Val Gly Ser Gln Gly Asp Trp Ser Leu
        275                 280                 285

Glu Met Gly Glu Lys Leu Leu Leu Ala Met Glu Asn Tyr Thr Ala Ile
    290                 295                 300

Pro Tyr Tyr Thr Met Ala Gln Asn Ile Asp Met Lys Gln Ala Ala Ile
305                 310                 315                 320

Pro Asp Phe Ser Ala Gly Ala Met Glu Asn Trp Gly Leu Leu Thr Tyr
                325                 330                 335

Arg Glu Ala Leu Ile Leu Tyr Asp Pro Leu Asn Ser Asn His His Tyr
            340                 345                 350

Arg Gln Arg Val Ala Asn Ile Val Ser His Glu Ile Ala His Met Trp
```

-continued

```
              355                 360                 365
    Phe Gly Asn Leu Val Thr Cys Ala Trp Trp Asp Asn Leu Trp Leu Asn
        370                 375                 380

Glu Gly Phe Ala Arg Phe Tyr Gln Tyr Tyr Leu Thr Ala Thr Val Asp
    385                 390                 395                 400

Pro Glu Leu Gly Tyr Glu Ile Arg Phe Ile Pro Glu Gln Leu Gln Val
                    405                 410                 415

Ala Met Phe Ser Asp Ser Val Asp Ser Ala His Ala Leu Thr Asp Thr
                420                 425                 430

Ser Val Asn Asp Pro Val Ala Val Ser Ala His Phe Ser Thr Ile Thr
            435                 440                 445

Tyr Ala Arg Gly Ala Ala Ile Leu Arg Met Thr Gln His Leu Leu Ser
        450                 455                 460

Tyr Asp Thr Phe Val Lys Gly Leu Arg Gln Tyr Leu Arg Ala Arg Gln
    465                 470                 475                 480

Phe Asp Val Ala Glu Pro Tyr His Leu Phe Ser Ala Leu Asp Ala Ala
                    485                 490                 495

Ala Ala Glu Asp Asn Ala Leu Ala Ala Tyr Thr Gly Ile Thr Ile Asp
                500                 505                 510

Ala Tyr Phe Arg Thr Trp Ser Glu Lys Ala Gly His Pro Leu Leu Ser
            515                 520                 525

Val Thr Val Asp His Glu Thr Gly Arg Met Thr Leu Val Gln Ala Arg
    530                 535                 540

Trp Glu Arg Asn Thr Gly Val Ser Arg Phe Pro Gly Leu Trp His Ile
    545                 550                 555                 560

Pro Ile Thr Trp Thr Arg Ala Gly Ala Pro Asp Phe Glu Asn Leu Lys
                    565                 570                 575

Pro Ser Gln Val Met Thr Gly Gln Ser Leu Val Ile Asp Arg Gly Thr
                580                 585                 590

Arg Gly Gln Glu Trp Val Ile Phe Asn Lys Gln Val Ser Gly Phe Tyr
            595                 600                 605

Arg Val Asn Tyr Asp Asn Thr Thr Trp Gly Leu Ile Thr Arg Ala Leu
        610                 615                 620

Arg Ser Ala Asn Arg Thr Val Ile His Glu Leu Ser Arg Ser Gln Ile
    625                 630                 635                 640

Val Asp Asp Val Phe Gln Leu Ala Arg Ser Gly Val Met Ser Tyr Gln
                    645                 650                 655

Arg Ala Leu Asn Ile Leu Ser Tyr Leu Arg Phe Glu Asp Ala Tyr Ala
                660                 665                 670

Pro Trp Leu Ser Ala Ile Ser Gly Phe Asn Trp Val Ile Arg Arg Phe
            675                 680                 685

Ala His Asp Ala Ala Asn Leu Gln Thr Leu Gln Asn Gln Ile Ile Gly
        690                 695                 700

Leu Ser Glu Ala Val Val Ala Arg Leu Gly Phe Thr Glu Val Ser Gly
    705                 710                 715                 720

Gly Thr Tyr Met Thr Asp Leu Gln Arg Leu His Val Met Gln Phe Leu
                    725                 730                 735

Cys Asn Val Gly His Gln Gln Cys Ile Asp Thr Gly Arg Gln Asn Phe
                740                 745                 750

Leu Asn Trp Arg Asn Gly Ser Phe Ile Pro Ala Asn Met Arg Pro Trp
            755                 760                 765

Val Tyr Cys Thr Gly Leu Arg Tyr Gly Ser Ala Glu Asp Phe Asn Tyr
    770                 775                 780
```

```
Phe Trp Asn Arg Tyr Ile Val Glu Asp Leu Ser Asn Glu Lys Val Val
785                 790                 795                 800

Met Leu Glu Ala Ala Gly Cys Thr Arg Asp Gln Ala Ser Leu Glu Lys
                805                 810                 815

Phe Leu Asn Ala Ile Val Ser Gly Asn Asp Val Arg Pro Gln Asp
            820                 825                 830

His Ser Ser Ala Leu Ser Ser Ala Ile Thr Ser Asn Asp Val Asn Thr
        835                 840                 845

Met Arg Ala Phe Asp Trp Leu Thr Lys Asn Val Asp Gln Ile Thr Arg
    850                 855                 860

Thr Leu Gly Ser Ile Thr Ser Pro Leu Asn Thr Ile Thr Ser Arg Leu
865                 870                 875                 880

Leu Thr Glu Ala Gln Met Thr Gln Val Gln Thr Trp Leu Asp Ala Asn
                885                 890                 895

Arg Asn Thr Ile Gly Ala Ala Tyr Asn Thr Gly Val Asn Gly Ile Ala
                900                 905                 910

Thr Ser Arg Ala Asn Leu Gln Trp Ser Ala Asn Arg Met Ser Glu Phe
            915                 920                 925

Leu Arg Phe Phe Glu Thr Gly Phe Val Asp Asp Val Pro Ser Glu Ala
    930                 935                 940

Thr Thr Val Ala Pro Pro Ala Glu Thr Thr Val Thr Pro Ser Thr Phe
945                 950                 955                 960

Pro Pro Thr Glu Ala Pro Ala Thr Thr Pro Ala Pro Gly Ser Gly Asn
                965                 970                 975

Ile Ala Ala Leu Ser Val Val Ser Leu Leu Val Thr Leu Ala Ile Asn
            980                 985                 990

Met Val Ala
    995

<210> SEQ ID NO 2
<211> LENGTH: 2988
<212> TYPE: DNA
<213> ORGANISM: Manduca sexta

<400> SEQUENCE: 2
atggtgaatc tcgggtttac cattttcttg ggggtcgccc ttctccaggg cgttcttact      60
ttgagcccca tacccgtccc agaagaagaa tgggccgaat ctccagaat gctgcgggac      120 ccgagctacc gcctgcctac taccacccgg ccaagacatt acgctgtgac cctgactcca     180
tactttgacg tggtacctgc tggtgtcagc agccttacca ccttcagctt tgacggcgag     240
gtcaccatct acatatcgcc cactcaagct aatgttaatg agatcgtcct ccactgcaat     300
gacttgacga tacagagtct gagggtaaca tatgttagtg gtaatagtga ggtggatatc     360
acggcaactg gacaaacttt tacgtgtgag atgccctaca gttttctcag aataaggacc     420
tctacgcctc tagtgatgaa ccaagagtat attatcagga gtaccttag aggcaacttg      480 cagactaaca tgagagggtt ctacagaagt tggtacgtcg atagaaccgg aaagagatgg     540
atggctacca ctcaacttca acccggacat gcgcgtcaag cgttcccttg ctacgatgag     600
cctggtttca aggccacctt cgacattact atgaacagag aagccgactt tagcccgacc     660
atatctaata tgcctattag ggccactacc acgctcacga atggacgtat tccgaaaaca     720
ttttccacca ctcccttgac atccacctat ctccttgcct tcatagtctc tcactatcag     780
gtcatttcta acaacaacaa tgcagcacgc ccttttagaa tctatgcacg taataatgta     840
```

```
gggagccagg gtgactggtc tcttgaaatg ggtgagaaac tgctattagc tatggagaat      900
tatactgcaa taccttatta cacgatggca caaaacattg atatgaaaca agccgccatt      960
cccgacttct ctgctggtgc tatggaaaac tggggtctct tgacatacag ggaagccctc     1020
atcttatacg acccccctcaa ttcgaaccat cactaccgtc agcgcgtagc gaacattgtc    1080
tcccacgaga tcgctcacat gtggttcggt aaccttgtca catgcgcatg gtgggataac     1140
ctttggctga acgaaggttt tgcgcggttc taccaatact accttactgc aacggtcgac     1200
ccagagctcg gttatgaaat tcgtttcatc ccagagcagc ttcaagtggc gatgttctct     1260
gactccgtag acagcgccca cgctcttact gacaccagtg ttaatgatcc tgttgctgtc     1320
agcgctcact tctcaacaat cacttacgcc aggggagccg ccatcctcag aatgacacag     1380
catttgttga gctatgacac cttcgtcaaa ggtcttaggc agtatctgcg tgctcgacaa     1440
tttgacgtcg ccgaacccta ccacctgttc tccgctttgg atgctgcggc tgctgaagac     1500
aatgctctcg ctgcctacac aggcatcact attgacgctt acttcaggac ttggtcagag     1560
aaggcgggac atcccttct ctcagttact gttgatcatg aaaccggccg tatgactctc      1620
gttcaggcaa gatgggagcg caataccggt gtgtctcgat cccgggcttt atggcatatc     1680
cctatcacat ggacaagggc tggagcccca gacttcgaaa acctgaagcc ctcgcaagtt     1740
atgactggac agtctttagt cattgaccgt ggtaccagag acaagagtg ggtcatcttc      1800
aacaagcaag tatcaggttt ctaccgtgtc aactacgata ataccacctg gggtctcatc     1860
acaagggctc tgaggtctgc gaacaggaca gttattcacg aattgagtcg ctctcagata     1920
gtagacgatg tcttccaact ggctagatcc ggcgtgatgt cataccaacg agcacttaac     1980
attctgtcct acttgagatt cgaagacgcg tacgcaccgt ggttgtccgc catcagcggg     2040
ttcaactggg tcatcaggag attcgcccat gacgccgcca atttacaaac tttacagaac     2100
caaatcatcg gactgagcga agctgtggtg gctcggcttg gcttcaccga agtatccggt     2160
ggtacttata tgaccgacct ccagaggttg catgtaatgc agtttctctg caatgtggga     2220
catcagcagt gcattgacac tggaagacag aacttcttga actggaggaa cggtagcttt     2280
atcccagcta acatgcgtcc atgggtgtac tgcactggtc ttcgttacgg ctctgctgag     2340
gacttcaatt acttctggaa tcgttacatc gtagaagatc tgtctaatga aaaggttgtg     2400
atgctcgaag cggccggttg cacgcgtgac caggccagct tggagaagtt cttgaacgct     2460
atcgtttctg gcaatgatga cgtcagacca caggatcatt cgagtgccct gagctcagct     2520
atcacatcca acgacgtcaa caccatgaga gcgttcgact ggttgaccaa gaatgtagat     2580
caaattacac gaactcttgg tagtatcacc tcgccgctga acaccatcac gagccgtctc     2640
ttgaccgagg cacagatgac tcaggtacaa acttggcttg acgcaaaccg taacaccatc     2700
ggcgctgcct acaacactgg cgtgaacggc atcgccacat cgagagctaa tctccagtgg     2760
tcggcgaaca gaatgtctga gttcctgcgc ttcttcgaaa ctgggttcgt cgacgatgtt     2820
cctagtgagg cgactactgt tgcgccccct gccgaaacta cggtgactcc ctctaccttc     2880
cctccgacgg aagcaccggc gactactcca gccccgggct caggaaacat cgccgctttg     2940
agcgttgtca gcctcctcgt cacacttgcc attaacatgg tagcgtaa                  2988
```

<210> SEQ ID NO 3
<211> LENGTH: 22
<212> TYPE: DNA
<213> ORGANISM: Manduca sexta

<400> SEQUENCE: 3

```
atttctttgg gggtcgccct tc                                              22

<210> SEQ ID NO 4
<211> LENGTH: 17
<212> TYPE: DNA
<213> ORGANISM: Manduca sexta

<400> SEQUENCE: 4
acgctaccat gttaatg                                                    17

<210> SEQ ID NO 5
<211> LENGTH: 17
<212> TYPE: DNA
<213> ORGANISM: Manduca sexta

<400> SEQUENCE: 5
tgctgtgtca ttctgag                                                    17

<210> SEQ ID NO 6
<211> LENGTH: 21
<212> TYPE: DNA
<213> ORGANISM: Manduca sexta

<400> SEQUENCE: 6
aggagattcg cccatgacgc c                                               21

<210> SEQ ID NO 7
<211> LENGTH: 20
<212> TYPE: DNA
<213> ORGANISM: Manduca sexta

<400> SEQUENCE: 7
aattaaccct cactaaaggg                                                 20

<210> SEQ ID NO 8
<211> LENGTH: 22
<212> TYPE: DNA
<213> ORGANISM: Manduca sexta

<400> SEQUENCE: 8
gtaatacgac tcactatagg gc                                              22

<210> SEQ ID NO 9
<211> LENGTH: 942
<212> TYPE: PRT
<213> ORGANISM: Manduca sexta

<400> SEQUENCE: 9

Met Tyr Ser Leu Ile Phe Leu Ala Leu Ile Gly Ala Ala Phe Gly Val
1               5                  10                  15

Pro Leu Ser Thr Asn Glu Asp Ser Thr Arg Asn Gln Asn Leu Ala Ala
            20                  25                  30

Leu Tyr Val Leu Pro Gln Thr Ser Tyr Pro Thr Phe Tyr Asp Val Arg
        35                  40                  45

Leu Phe Ile Asp Pro Gly Tyr Thr Glu Ala Phe His Gly Asn Val Ser
    50                  55                  60

Ile Arg Ile Ile Pro Asn Ile Asn Ile Asp Gln Ile Thr Ile His Ala
65                  70                  75                  80

Met Ala Met Arg Ile Asp Ser Ile Arg Val Val Ser Asp Val Asn Pro
                85                  90                  95
```

-continued

```
Asn Glu Asp Leu Phe Ser Asp Phe Thr Leu Ala Thr Asp Thr His
                100                 105                 110

Leu Leu Thr Ile Arg Leu Thr Arg Asn Ile Thr Ala Leu Gln Pro His
        115                 120                 125

Val Ile His Ile Asp Tyr Val Ala Gln Tyr Ala Asp Asp Met Phe Gly
    130                 135                 140

Val Tyr Val Ser Thr Tyr Glu Glu Asn Gly Arg Thr Val Asn Leu Val
145                 150                 155                 160

Thr Ser Gln Leu Gln Pro Thr Phe Ala Arg Arg Ala Phe Pro Cys Tyr
                165                 170                 175

Asp Glu Pro Ala Leu Lys Ala Val Phe Arg Thr Thr Ile Tyr Ala Pro
                180                 185                 190

Ala Ala Tyr Ala Thr Val Arg Ser Asn Thr Pro Glu Arg Arg Asp Ser
            195                 200                 205

Leu Lys Pro Asn Glu Pro Gly Tyr Val Lys His Glu Phe Glu Asp Thr
        210                 215                 220

Leu Val Met Ser Thr Tyr Leu Ile Ala Tyr Leu Val Ser Asn Phe Asn
225                 230                 235                 240

Tyr Ile Glu Asn Ser Gln Asn Pro Ile Tyr Pro Ile Pro Phe Arg Val
                245                 250                 255

Tyr Ser Arg Pro Gly Thr Gln Asn Thr Ala Glu Phe Ala Leu Glu Phe
            260                 265                 270

Gly Gln Gln Asn Met Ile Ala Leu Glu Glu Tyr Thr Glu Phe Pro Tyr
        275                 280                 285

Ala Phe Pro Lys Ile Asp Lys Ala Ala Val Pro Asp Phe Ala Ala Gly
    290                 295                 300

Ala Met Glu Asn Trp Gly Leu Val Ile Tyr Arg Glu Val Ala Leu Leu
305                 310                 315                 320

Val Arg Glu Gly Val Thr Thr Thr Ser Val Lys Gln Asn Ile Gly Arg
                325                 330                 335

Ile Ile Cys His Glu Asn Thr His Met Trp Phe Gly Asn Glu Val Gly
            340                 345                 350

Pro Met Ser Trp Thr Tyr Thr Trp Leu Asn Glu Gly Phe Ala Asn Phe
        355                 360                 365

Phe Glu Asn Tyr Ala Thr Asp Phe Val Arg Pro Gln Trp Arg Met Met
    370                 375                 380

Asp Gln Phe Val Ile Ala Met Gln Asn Val Phe Pro Val Arg Arg Cys
385                 390                 395                 400

Ser Lys Cys Gln Pro His Asp Ala Pro Gly Leu Tyr Ser Phe Pro Asp
                405                 410                 415

His Arg Tyr Phe Gln Arg Arg Leu Pro Glu Val Trp Phe Arg Tyr
            420                 425                 430

Ser Asp Val Ala Ala Phe His Asp Thr Arg Asp Phe Gln Glu Arg Ser
        435                 440                 445

Gly His Leu His Gln Ser Gln Leu Ser Arg Pro Ala Ala Pro Ser Asp
    450                 455                 460

Leu Tyr Val Ala Leu Gln Gln Ala Leu Asp Glu Ser Ser His Arg Ile
465                 470                 475                 480

Pro Lys Pro Ile Ser Thr Ile Met Thr Glu Trp Ser Thr Gln Gly Gly
                485                 490                 495

Phe Pro Val Leu Thr Val Arg Thr Ala Pro Asn Ala Asp Ser Val
            500                 505                 510

Phe Val Ala Gln Glu Arg Tyr Leu Thr Asp Arg Ser Leu Thr Ser Thr
```

-continued

```
                515                 520                 525
Asp Arg Trp His Val Pro Val Asn Trp Val Ile Ser Ser Asn Val Asn
        530                 535                 540
Phe Ser Asp Thr Ser Pro Gln Ala Trp Ile Leu Pro Thr Phe Pro Ala
545                 550                 555                 560
Thr Ala Val Asp Val Pro Gly Leu Ser Asn Ala Asp Trp Tyr Ile Phe
                565                 570                 575
Asn Lys Gln Gln Thr Gly Tyr Tyr Arg Val Asn Tyr Asp Val Glu Asn
        580                 585                 590
Trp Val Ala Leu Ala Arg Val Leu Asn Asn Ser His Glu Ile Ile His
                595                 600                 605
Val Leu Asn Arg Ala Gln Ile Val Asp Asp Ala Phe Asn Leu Ala Arg
        610                 615                 620
Asn Gly Arg Leu His Tyr Lys Asn Ala Phe Glu Ile Ser Arg Tyr Leu
625                 630                 635                 640
Glu Met Glu Lys Asp Tyr Ile Pro Trp Ala Ala Asn Pro Ala Phe
                645                 650                 655
Asn Tyr Leu Asp Ile Val Leu Ser Gly Ala Asn Ser Tyr Asn Leu Tyr
                660                 665                 670
Arg Tyr Tyr Leu Leu Asn Leu Thr Ala Pro Met Phe Glu Asp Leu Gly
        675                 680                 685
Phe Asp Val Lys Ser Gly Glu Glu Phe Val Thr Pro Tyr His Arg Asn
690                 695                 700
Ile Ile Leu Asp Ile Asn Cys Arg Phe Gly Asn Gln Arg Cys Ile Ser
705                 710                 715                 720
Arg Ala Gln Glu Ile Leu Gln Ala Phe Lys Asn Asn Pro Asn Gln Arg
                725                 730                 735
Pro Asn Pro Asp Ile Gln Thr Leu Val Tyr Cys Ser Ser Leu Arg Ala
                740                 745                 750
Gly Asn Val Glu Asn Phe Asn Phe Leu Trp Asn Met Tyr Leu Gly Thr
        755                 760                 765
Ser Asp Ser Ser Glu Gln Ser Ile Leu Leu Ser Ala Leu Gly Cys Thr
        770                 775                 780
Ser Asn Ala Glu Arg Arg Asn Phe Tyr Leu Asn Gln Ile Ile Asp Asp
785                 790                 795                 800
Asn Ser Ala Val Arg Glu Gln Asp Arg His Ser Ile Ala Val Ser Val
                805                 810                 815
Ile Asn Ser Ser Pro Glu Gly Met Asn Val Ala Leu Asp Phe Val Val
                820                 825                 830
Glu Asn Phe His Arg Ile Gln Pro Arg Val Gln Ala Leu Thr Gly Thr
        835                 840                 845
Thr Asn Ile Leu Asn Thr Phe Ala Arg Arg Leu Thr Thr Ser Ala His
        850                 855                 860
Asn Glu Lys Ile Asp Glu Leu Val Arg Arg His Glu Ser Ile Phe Ser
865                 870                 875                 880
Ala Gly Glu Arg Ala Ser Ile Ala Ala Ile Arg Glu Asn Ile Ala Ala
                885                 890                 895
Ser Ile Ala Trp Ser Asn Ser Asn Ala Gly Ile Val Glu Asn Trp Leu
                900                 905                 910
Lys Glu Asn Tyr Gly Pro Pro Ser Gly Ala Lys Ser Leu Thr Ala Gly
        915                 920                 925
Leu Leu Val Leu Ile Ser Leu Phe Val Ala Ile Phe Asn His
        930                 935                 940
```

<210> SEQ ID NO 10
<211> LENGTH: 946
<212> TYPE: PRT
<213> ORGANISM: Plutella xylostella

<400> SEQUENCE: 10

```
Met Arg Leu Leu Ile Cys Leu Thr Leu Leu Gly Leu Val Cys Gly Asn
1               5                   10                  15

Pro Val Gln Leu Thr Asp Asn Ser Ile Ala Leu Gln Asn Thr Tyr Asp
            20                  25                  30

Asn Tyr Val Leu Pro Gly Glu Ser Phe Pro Thr Phe Tyr Asp Val Gln
        35                  40                  45

Leu Phe Phe Asp Pro Glu Tyr Glu Ala Ser Phe Asn Gly Thr Val Ala
    50                  55                  60

Ile Arg Val Val Pro Arg Ile Ala Thr Gln Glu Ile Val Leu His Ala
65                  70                  75                  80

Met Glu Met Glu Ile Leu Ser Ile Arg Ala Tyr Ser Asp Leu Pro Ser
                85                  90                  95

Asp Asp Asn Leu Asn Glu Asn Leu Phe Ser Ser Tyr Thr Leu Ala Thr
            100                 105                 110

Asp Asp Thr His Leu Leu Lys Ile Gln Phe Thr Arg Val Leu Asp Ala
        115                 120                 125

Leu Gln Pro Ile Thr Val Glu Ile Ser Tyr Ser Ala Gln Tyr Ala Pro
    130                 135                 140

Asn Met Phe Gly Val Tyr Val Ser Arg Tyr Val Glu Asn Gly Ala Thr
145                 150                 155                 160

Val Ser Leu Val Thr Ser Gln Leu Gln Pro Thr Phe Ala Arg Arg Ala
                165                 170                 175

Phe Pro Cys Tyr Asp Glu Pro Ala Leu Lys Ala Val Phe Arg Thr Thr
            180                 185                 190

Ile Tyr Ala Pro Pro Ala Tyr Asn Val Val Glu Thr Asn Met Pro Leu
        195                 200                 205

Arg Thr Asp Ser Leu Lys Ser Asp Arg Pro Gly Phe Thr Lys His Glu
    210                 215                 220

Phe Gln Asp Thr Leu Val Met Ser Ser Tyr Leu Leu Ala Tyr Leu Val
225                 230                 235                 240

Ser Lys Phe Asp Tyr Ile Ser Asn Glu Asn Asn Pro Thr Tyr Asp Lys
                245                 250                 255

Ser Met Lys Val Phe Ser Arg Pro Gly Thr Gln Asn Thr Ala Glu Phe
            260                 265                 270

Ala Leu Asp Phe Gly Gln Lys Asn Met Val Glu Leu Glu Lys Tyr Thr
        275                 280                 285

Glu Phe Pro Tyr Ala Phe Pro Lys Ile Asp Lys Val Ala Val Pro Asp
    290                 295                 300

Phe Ala Ala Gly Ala Met Glu Asn Trp Gly Leu Val Ile Tyr Arg Glu
305                 310                 315                 320

Ile Ala Leu Leu Val Gln Glu Gly Val Thr Thr Thr Ser Thr Leu Gln
                325                 330                 335

Gly Ile Gly Arg Ile Ile Ser His Glu Asn Thr His Gln Trp Phe Gly
            340                 345                 350

Asn Glu Val Gly Pro Asp Ser Trp Thr Tyr Thr Trp Leu Asn Glu Gly
        355                 360                 365

Phe Ala Asn Phe Phe Glu Ser Phe Ala Thr Asp Leu Val Leu Pro Glu
```

```
              370                 375                 380
Trp Arg Met Met Asp Gln Phe Val Ile Asn Met Gln Asn Val Phe Gln
385                 390                 395                 400

Ser Asp Ala Val Leu Ser Val Asn Pro Ile Thr Phe Glu Val Arg Thr
                405                 410                 415

Pro Ser Gln Ile Leu Gly Thr Phe Asn Ser Val Ala Tyr Gln Lys Ser
                420                 425                 430

Gly Ser Val Ile Arg Met Met Gln His Phe Leu Thr Pro Glu Ile Phe
                435                 440                 445

Arg Lys Ser Leu Ala Leu Tyr Ile Ser Arg Met Ser Arg Lys Ala Ala
        450                 455                 460

Lys Pro Thr Asp Leu Phe Glu Ala Ile Gln Glu Val Val Asp Ala Ser
465                 470                 475                 480

Asp His Ser Ile Arg Trp Arg Leu Ser Ile Ile Met Asn Arg Trp Thr
                485                 490                 495

Gln Gln Gly Gly Phe Pro Val Val Thr Val Arg Arg Ser Ala Pro Ser
                500                 505                 510

Ala Gln Ser Phe Val Ile Thr Gln Arg Arg Phe Leu Thr Asp Ser Thr
        515                 520                 525

Gln Glu Ser Asn Thr Val Trp Asn Val Pro Leu Asn Trp Val Leu Ser
        530                 535                 540

Thr Asp Val Asn Phe Asn Asp Thr Arg Pro Met Ala Trp Leu Pro Pro
545                 550                 555                 560

Gln Leu Ala Ala Glu Ala Val Gln Val Pro Gly Leu Gln Asn Ala Glu
                565                 570                 575

Trp Phe Ile Val Asn Lys Gln Gln Thr Gly Tyr Tyr Arg Val Asn Tyr
                580                 585                 590

Asp Pro Glu Asn Trp Arg Ala Leu Ala Lys Val Leu Asn Asp Thr His
                595                 600                 605

Glu Ile Ile His Leu Leu Asn Arg Ala Gln Leu Ile Asp Asp Ser Phe
        610                 615                 620

Asn Leu Ala Arg Asn Gly Arg Leu Asp Tyr Ser Leu Ala Phe Asp Leu
625                 630                 635                 640

Ser Arg Tyr Leu Val Gln Glu Arg Asp Tyr Ile Pro Trp Ala Ala Ala
                645                 650                 655

Asn Ala Ala Phe Asn Tyr Leu Asn Ser Val Leu Ser Gly Ser Ser Val
                660                 665                 670

His Pro Leu Phe Gln Glu Tyr Leu Leu Phe Leu Thr Ala Pro Leu Tyr
            675                 680                 685

Gln Arg Leu Gly Phe Asn Ala Ala Thr Gly Glu Glu His Val Thr Pro
        690                 695                 700

Phe His Arg Asn Ile Ile Leu Asn Ile Asn Cys Leu His Gly Asn Glu
705                 710                 715                 720

Asp Cys Val Ser Thr Ala Glu Thr Leu Leu Gln Asn Phe Arg Asp Asn
                725                 730                 735

Pro Thr Gln Thr Leu Asn Pro Asp Ile Gln Thr Thr Val Phe Cys Ser
            740                 745                 750

Gly Leu Arg Gly Gly Asp Val Asp Asn Phe Asn Phe Leu Trp Ala Arg
        755                 760                 765

Tyr Thr Ala Thr Gln Asp Ser Ser Glu Gln Ser Ile Leu Leu Asn Ala
        770                 775                 780

Leu Gly Cys Thr Ser Asn Ala Asp Arg Arg Asp Phe Leu Phe Ser Gln
785                 790                 795                 800
```

```
Val Ile Ala Ser Asp Ser Gln Val Arg Glu Gln Asp Arg His Ser Val
                805                 810                 815
Leu Val Ser Ala Ile Asn Ser Gly Pro Asp Asn Met Asn Ala Ala Leu
            820                 825                 830
Asp Phe Val Leu Glu Asn Phe Ala Asn Ile Gln Pro Asn Val Gln Gly
            835                 840                 845
Leu Thr Gly Thr Thr Asn Ile Leu Asn Ala Phe Ala Arg Thr Leu Thr
        850                 855                 860
Thr Gln Glu His Ala Asn Lys Ile Asp Glu Phe Ser Asn Lys Tyr Ala
865                 870                 875                 880
Asn Val Phe Thr Ala Gly Glu Met Ala Ser Val Ala Ala Ile Lys Glu
                885                 890                 895
Asn Ile Ala Ala Ser Ile Thr Trp Asn Ser Gln Asn Ala Ala Thr Val
            900                 905                 910
Glu Ala Trp Leu Arg Lys Asn Phe Gly Thr Asp Gly Ala Ser Thr Val
            915                 920                 925
Ser Ala Ser Ile Thr Ile Ile Ser Ala Met Val Ala Ile Tyr Asn
        930                 935                 940
Ile Leu
945

<210> SEQ ID NO 11
<211> LENGTH: 990
<212> TYPE: PRT
<213> ORGANISM: Manduca sexta

<400> SEQUENCE: 11

Phe Thr Ile Phe Leu Gly Val Ala Leu Leu Gln Gly Val Leu Thr Leu
1               5                   10                  15
Ser Pro Ile Pro Val Pro Glu Glu Trp Ala Glu Phe Ser Arg Met
            20                  25                  30
Leu Arg Asp Pro Ser Tyr Arg Leu Pro Thr Thr Thr Arg Pro Arg His
        35                  40                  45
Tyr Ala Val Thr Leu Thr Pro Tyr Phe Asp Val Val Pro Ala Gly Val
    50                  55                  60
Ser Gly Leu Thr Thr Phe Ser Phe Asp Gly Glu Val Thr Ile Tyr Ile
65                  70                  75                  80
Ser Pro Thr Gln Ala Asn Val Asn Glu Ile Val Leu His Cys Asn Asp
                85                  90                  95
Leu Thr Ile Gln Ser Leu Arg Val Thr Tyr Val Ser Gly Asn Ser Glu
            100                 105                 110
Val Asp Ile Thr Ala Thr Gly Gln Thr Phe Thr Cys Glu Met Pro Tyr
        115                 120                 125
Ser Phe Leu Arg Ile Arg Thr Ser Thr Pro Leu Val Met Asn Gln Glu
    130                 135                 140
Tyr Ile Ile Arg Ser Thr Phe Arg Gly Asn Leu Gln Thr Asn Met Arg
145                 150                 155                 160
Gly Phe Tyr Arg Ser Trp Tyr Val Asp Arg Thr Gly Lys Arg Trp Met
                165                 170                 175
Ala Thr Thr Gln Phe Gln Pro Gly His Ala Arg Gln Ala Phe Pro Cys
            180                 185                 190
Tyr Asp Glu Pro Gly Phe Lys Ala Thr Phe Asp Ile Thr Met Asn Arg
        195                 200                 205
Glu Ala Asp Phe Ser Pro Thr Ile Ser Asn Met Pro Ile Arg Ala Thr
```

-continued

```
              210                 215                 220
Thr Thr Leu Thr Asn Gly Arg Ile Ser Glu Thr Phe Phe Thr Thr Pro
225                 230                 235                 240

Leu Thr Ser Thr Tyr Leu Leu Ala Phe Ile Val Ser His Tyr Gln Val
                245                 250                 255

Ile Ser Asn Asn Asn Ala Ala Arg Pro Phe Arg Ile Tyr Ala Arg
            260                 265                 270

Asn Asn Val Gly Ser Gln Gly Asp Trp Ser Leu Glu Met Gly Glu Lys
                275                 280                 285

Leu Leu Leu Ala Met Glu Asn Tyr Thr Ala Ile Pro Tyr Tyr Thr Met
            290                 295                 300

Ala Gln Asn Leu Asp Met Lys Gln Ala Ala Ile Pro Asp Phe Ser Ala
305                 310                 315                 320

Gly Ala Met Glu Asn Trp Gly Leu Leu Thr Tyr Arg Glu Ala Leu Ile
                325                 330                 335

Leu Tyr Asp Pro Leu Asn Ser Asn His His Tyr Arg Gln Arg Val Ala
                340                 345                 350

Asn Ile Val Ser His Glu Ile Ala His Met Trp Phe Gly Asn Leu Val
                355                 360                 365

Thr Cys Ala Trp Trp Asp Asn Leu Trp Leu Asn Glu Gly Phe Ala Arg
370                 375                 380

Phe Ser Gln Tyr Tyr Leu Thr Ala Thr Val Asp Pro Glu Leu Gly Tyr
385                 390                 395                 400

Glu Ile Arg Phe Ile Pro Glu Gln Leu Gln Val Ala Met Phe Ser Asp
                405                 410                 415

Ser Val Asp Ser Ala His Ala Leu Thr Asp Thr Ser Val Asn Asp Pro
                420                 425                 430

Val Ala Val Ser Ala His Phe Ser Thr Ile Thr Tyr Ala Arg Gly Ala
                435                 440                 445

Ala Ile Leu Arg Met Thr Gln His Leu Leu Ser Tyr Asp Thr Phe Val
450                 455                 460

Lys Gly Leu Arg Gln Tyr Leu Arg Ala Arg Gln Phe Asp Val Ala Glu
465                 470                 475                 480

Pro Tyr His Leu Phe Ser Ala Leu Asp Ala Ala Ala Glu Asp Asn
                485                 490                 495

Ala Leu Ala Ala Tyr Arg Gly Ile Thr Ile Asp Ala Tyr Phe Arg Thr
                500                 505                 510

Trp Ser Glu Lys Ala Gly His Pro Leu Leu Ser Val Thr Val Asp His
            515                 520                 525

Glu Ser Gly Arg Met Thr Leu Val Gln Ala Arg Trp Glu Arg Asn Thr
            530                 535                 540

Gly Val Ser Arg Phe Pro Gly Leu Trp His Ile Pro Ile Thr Trp Thr
545                 550                 555                 560

Arg Ala Gly Ala Pro Asp Phe Glu Asn Leu Lys Pro Ser Gln Val Met
                565                 570                 575

Thr Gly Gln Ser Leu Val Ile Asp Arg Gly Thr Arg Gly Gln Glu Trp
                580                 585                 590

Val Ile Phe Asn Lys Gln Val Ser Gly Phe Tyr Arg Val Asn Tyr Asp
                595                 600                 605

Asn Thr Thr Trp Gly Leu Ile Thr Arg Ala Leu Arg Ser Ala Asn Arg
            610                 615                 620

Thr Val Ile His Glu Leu Ser Arg Ser Gln Ile Val Asp Asp Val Phe
625                 630                 635                 640
```

-continued

```
Gln Leu Ala Arg Ser Gly Val Met Ser Tyr Gln Arg Ala Leu Asn Ile
                645                 650                 655
Leu Ser Tyr Leu Arg Phe Glu Asp Ala Tyr Ala Pro Trp Leu Ser Ala
            660                 665                 670
Ile Ser Gly Phe Asn Trp Val Ile Arg Arg Phe Ala His Asp Ala Ala
        675                 680                 685
Asn Leu Gln Thr Leu Gln Asn Gln Ile Ile Gly Leu Ser Glu Ala Val
    690                 695                 700
Val Ala Arg Leu Gly Phe Thr Glu Val Ser Gly Gly Thr Tyr Met Thr
705                 710                 715                 720
Asp Leu Gln Arg Leu His Val Met Gln Phe Leu Cys Asn Val Gly His
                725                 730                 735
Gln Gln Cys Ile Asp Ala Gly Arg Gln Asn Phe Leu Asn Trp Arg Asn
            740                 745                 750
Gly Ser Phe Ile Pro Ala Asn Met Arg Pro Trp Val Tyr Cys Thr Gly
        755                 760                 765
Leu Arg Tyr Gly Ser Ala Glu Asp Phe Asn Tyr Phe Trp Asn Arg Tyr
    770                 775                 780
Ile Val Glu Asp Leu Ser Asn Glu Lys Val Val Met Leu Glu Ala Ala
785                 790                 795                 800
Gly Cys Thr Arg Asp Gln Ala Ser Leu Glu Lys Phe Leu Asn Ala Ile
                805                 810                 815
Val Ser Gly Asn Asp Asp Val Arg Pro Gln Asp His Ser Ser Ala Leu
            820                 825                 830
Ser Ser Ala Ile Thr Ser Asn Asp Val Asn Thr Met Arg Ala Phe Asp
        835                 840                 845
Trp Leu Thr Lys Asn Val Asp Gln Ile Thr Arg Thr Leu Gly Ser Ile
    850                 855                 860
Thr Ser Pro Leu Asn Thr Ile Thr Ser Arg Leu Leu Thr Glu Ala Gln
865                 870                 875                 880
Met Thr Gln Val Gln Thr Trp Leu Asp Ala Asn Arg Asn Thr Ile Gly
                885                 890                 895
Ala Ala Tyr Asn Thr Gly Val Asn Gly Ile Ala Thr Ser Arg Ala Asn
            900                 905                 910
Leu Gln Trp Ser Ala Asn Arg Met Ser Glu Phe Leu Arg Phe Phe Glu
        915                 920                 925
Thr Gly Phe Val Asp Asp Val Pro Ser Glu Ala Thr Val Ala Pro
    930                 935                 940
Pro Ala Glu Thr Thr Val Thr Pro Ser Thr Phe Pro Pro Thr Val Ala
945                 950                 955                 960
Pro Ala Thr Thr Pro Ala Pro Gly Ser Gly Asn Ile Ala Ala Leu Ser
                965                 970                 975
Val Val Ser Leu Leu Val Thr Leu Ala Ile Asn Met Val Ala
            980                 985                 990

<210> SEQ ID NO 12
<211> LENGTH: 986
<212> TYPE: PRT
<213> ORGANISM: Bombyx mori

<400> SEQUENCE: 12

Ala Arg Glu Trp His Leu Ala Gly Phe Thr Ser Ser Trp Ala Tyr Phe
1               5                   10                  15
Leu Gln Thr Ser Leu Thr Leu Ser Pro Ile Pro Val Pro Glu Asp Glu
```

-continued

```
                    20                  25                  30
Trp Val Glu Phe Ala Arg Met Leu Arg Asp Pro Ala Phe Arg Leu Pro
                35                  40                  45
Thr Thr Thr Arg Pro Arg His Tyr Gln Val Thr Leu Thr Pro Tyr Phe
             50                  55                  60
Asp Val Pro Ala Asn Val Asn Pro Phe Thr Phe Asp Gly Glu Val
 65                  70                  75                  80
Thr Ile Tyr Thr Ser Pro Thr Val Ala Asn Val Asn Glu Val Val Ile
                 85                  90                  95
His Cys Asn Asp Leu Thr Ile Gln Ser Leu Ser Ile Gly Tyr Gln Ser
                100                 105                 110
Gly Thr Asp Val Val Asp Ile Thr Ala Thr Gly Gln Thr Phe Ala Cys
                115                 120                 125
Glu Met Pro Phe Ser Phe Leu Arg Ile Arg Thr Thr Glu Ala Leu Val
        130                 135                 140
Leu Asn Arg Glu Tyr Ile Ile Lys Ser Thr Phe Arg Gly Asn Leu Gln
145                 150                 155                 160
Thr Asn Met Arg Gly Phe Tyr Arg Ser Trp Tyr Val Asp Ser Thr Gly
                165                 170                 175
Arg Arg Trp Met Gly Thr Thr Gln Phe Gln Pro Gly His Ala Arg Gln
            180                 185                 190
Ala Phe Pro Cys Tyr Asp Glu Pro Gly Phe Lys Ala Thr Phe Asp Ile
            195                 200                 205
Thr Met Asn Arg Glu Glu Ser Phe Ser Pro Thr Ile Ser Asn Met Pro
        210                 215                 220
Ile Arg Thr Thr Asn Thr Leu Ala Asn Gly Arg Val Ser Glu Thr Phe
225                 230                 235                 240
Trp Thr Thr Pro Val Thr Ser Thr Tyr Leu Leu Ala Phe Ile Val Ser
                245                 250                 255
His Tyr Thr Val Val Ser Thr Asn Asn Asn Ala Leu Arg Pro Phe Asp
            260                 265                 270
Ile Tyr Ala Arg Asn Asn Val Gly Arg Thr Gly Asp Trp Ser Leu Glu
        275                 280                 285
Ile Gly Glu Lys Leu Leu Glu Ala Met Glu Ala Tyr Thr Gln Ile Pro
    290                 295                 300
Tyr Tyr Thr Met Ala Glu Asn Ile Asn Met Lys Gln Ala Ala Ile Pro
305                 310                 315                 320
Asp Phe Ser Ala Gly Ala Met Glu Asn Trp Gly Leu Leu Thr Tyr Arg
                325                 330                 335
Glu Ala Leu Ile Leu Tyr Asp Pro Leu Asn Ser Asn His Phe Tyr Lys
            340                 345                 350
Gln Arg Val Ala Asn Ile Val Ala His Glu Ile Ala His Met Trp Phe
            355                 360                 365
Gly Asn Leu Val Thr Cys Ala Trp Trp Asp Asn Leu Trp Leu Asn Glu
        370                 375                 380
Gly Phe Ala Arg Phe Tyr Gln Tyr Tyr Leu Thr Ala Ser Val Ala Pro
385                 390                 395                 400
Glu Leu Gly Tyr Glu Thr Arg Phe Ile Val Glu Gln Val Gln Met Ala
                405                 410                 415
Met Phe Ser Asp Ser Val Asp Thr Ala His Ala Leu Thr Asp Leu Asn
            420                 425                 430
Val Asn Asp Pro Thr Thr Val Ser Ala His Phe Ser Thr Ile Thr Tyr
        435                 440                 445
```

```
Ala Arg Gly Ala Ala Ile Leu Arg Met Thr Gln His Leu Leu Gly Val
    450                 455                 460

Glu Thr Phe Val Lys Gly Leu Arg Asn Tyr Leu Arg Glu Arg His Ser
465                 470                 475                 480

Met Leu Leu Ser Ser Ser Leu Phe Thr Ala Leu Asp Ala Ala Val
                485                 490                 495

Glu Asp Gly Ala Leu Asn Gly Tyr Gly Gly Ile Thr Ile Asp Thr Tyr
            500                 505                 510

Phe Arg Thr Trp Ser Glu Lys Ala Gly His Pro Leu Leu Thr Val Thr
            515                 520                 525

Ile Lys Pro Glu Asn Trp Gly Asn Asp Cys Thr Gln Glu Arg Trp Glu
    530                 535                 540

Arg Asn Thr Gly Val Ser Gln Phe Pro Ser Leu Trp His Ile Pro Ile
545                 550                 555                 560

Thr Trp Thr Arg Ala Gly Ala Pro Glu Phe Glu Asp Leu Lys Pro Ser
                565                 570                 575

Gln Phe Ile Ser Gln Gln Val Thr Ser Ile Asn Arg Gly Thr Thr Gly
                580                 585                 590

Leu Glu Trp Val Ile Phe Asn Lys Gln Glu Ala Gly Phe Tyr Arg Val
            595                 600                 605

Lys Tyr Asp Asp Thr Asn Trp Ala Leu Leu Thr Arg Ala Leu Arg Ser
    610                 615                 620

Ser Ser Arg Thr Ala Ile His Gln Leu Asn Arg Ala Gln Ile Val Asp
625                 630                 635                 640

Asp Ile Phe Gln Leu Ala Arg Ala Asn Val Met Lys Tyr Asn Arg Ala
                645                 650                 655

Phe Asn Ile Leu Ser Phe Leu Gln Phe Glu Asp Glu Tyr Ala Pro Trp
                660                 665                 670

Leu Ala Ala Ile Ser Gly Phe Asn Phe Leu Ile Arg Arg Leu Ala His
            675                 680                 685

Asp Ser Thr Asn Ala Ala Leu Leu Gln Lys Leu Ile Leu Glu Leu Ser
    690                 695                 700

Pro Ala Val Val Ala Lys Leu Gly Tyr Leu Glu Pro Glu Asn Gly Ser
705                 710                 715                 720

Tyr Met Thr Asp Leu Gln Arg Met Tyr Val Met Glu Phe Leu Cys Asn
                725                 730                 735

Val Gly Pro Glu Cys Asn Asn Phe Gly Thr Gln Ala Phe Arg Arg Trp
            740                 745                 750

Ser Thr Gly Thr Phe Ile Pro Ala Asn Met Arg Pro Trp Val Tyr Cys
            755                 760                 765

Ala Gly Leu Arg His Gly Thr Ala Glu Asp Phe Asn Phe Trp Asn
    770                 775                 780

Arg Tyr Leu Gln Glu Asp Leu Ser Ser Glu Lys Val Val Met Leu Asn
785                 790                 795                 800

Val Ala Gly Cys Thr Thr Asp Gln Ala Ser Leu Asn Arg Phe Leu Asp
                805                 810                 815

Ala Ile Val Ser Gly Asn Asp Asp Ile Arg Pro Gln Asp Tyr Asn Ala
            820                 825                 830

Ala Leu Thr Ser Ala Ile Thr Ser Asn Glu Ile Asn Thr Leu Arg Ala
            835                 840                 845

Phe Gln Trp Leu Arg Asn Asn Val Asp Gln Ala Thr Arg Thr Leu Gly
    850                 855                 860
```

```
Ser Val Ser Thr Ile Leu Asn Thr Ile Ile Gly Arg Leu Leu Asn Glu
865                 870                 875                 880

Glu Gln Ile Asn Glu Val Ser Asn Trp Leu Thr Ala Asn Gln Asn Thr
                885                 890                 895

Leu Gly Ala Thr Tyr Ser Thr Ala Leu Arg Ala Ile Glu Thr Thr Arg
            900                 905                 910

Ser Asn Leu Val Trp Ser Gln Gln Arg Ile Ser Glu Phe Thr Asn Tyr
            915                 920                 925

Phe Glu Ser Gly Tyr Val Glu Asp Val Ile Glu Ile Thr Glu Ala
            930                 935                 940

Pro Pro Thr Ala Pro Pro Thr Ala Pro Thr Glu Ala Pro Ala Val
945             950              955                 960

Thr Pro Ala Pro Asp Ser Ala Asn Val Ala Leu Ser Phe Ile Thr
                965                 970                 975

Leu Ile Ile Thr Leu Ala Val Asn Leu Ala
            980                 985

<210> SEQ ID NO 13
<211> LENGTH: 1009
<212> TYPE: PRT
<213> ORGANISM: Heliothis virescens

<400> SEQUENCE: 13

Met Ala Ala Ile Lys Leu Leu Val Leu Ser Leu Ala Cys Ala Cys Val
1               5                   10                  15

Ile Ala His Ser Pro Ile Pro Pro Ala Ser Arg Thr Ile Phe Leu Asp
                20                  25                  30

Glu Arg Leu Glu Gly Gly Ala Phe Glu Asn Ile Asp Ala Phe Glu Asn
            35                  40                  45

Ile Glu Leu Ser Asn Val Val Ala Ser Pro Tyr Arg Leu Pro Thr Thr
        50                  55                  60

Thr Val Pro Thr His Tyr Lys Ile Leu Trp Ile Ile Asp Ile His Gln
65                  70                  75                  80

Pro Val Gln Thr Tyr Ser Gly Asn Val Val Ile Thr Leu His Ala Thr
                85                  90                  95

Gln Ala Gln Val Asn Glu Ile Val Ile His Ser Asp His Met Thr Leu
            100                 105                 110

Ser Ser Val Val Leu Arg Gln Gly Asp Thr Val Ile Pro Thr Thr Pro
        115                 120                 125

Thr Ala Gln Pro Glu Tyr His Phe Leu Arg Val Lys Leu Asn Asp Gly
130                 135                 140

Tyr Leu Ala Tyr Asn Ala Asp Asn Ala Val Leu Tyr Thr Leu Ser Ile
145                 150                 155                 160

Asp Phe Thr Ala Pro Met Arg Asp Asp Met Tyr Gly Ile Tyr Asn Ser
                165                 170                 175

Trp Tyr Arg Asn Leu Pro Asp Asp Ala Asn Val Arg Trp Met Ala Thr
            180                 185                 190

Thr Gln Phe Gln Ala Thr Ala Ala Arg Tyr Ala Phe Pro Cys Tyr Asp
        195                 200                 205

Glu Pro Gly Phe Lys Ala Lys Phe Asp Val Thr Ile Arg Arg Pro Val
210                 215                 220

Gly Tyr Ser Ser Trp Phe Cys Thr Arg Gln Lys Gly Ser Gly Pro Ser
225                 230                 235                 240

Thr Val Ala Gly Tyr Glu Glu Asp Glu Tyr His Thr Thr Pro Thr Met
                245                 250                 255
```

-continued

```
Ser Thr Tyr Leu Leu Ala Leu Ile Val Ser Glu Tyr Thr Ser Leu Pro
        260                 265                 270

Ala Thr Asn Ala Ala Gly Glu Ile Leu His Glu Val Ile Ala Arg Pro
        275                 280                 285

Gly Ala Ile Asn Asn Gly Gln Ala Val Tyr Ala Gln Arg Val Gly Gln
        290                 295                 300

Ala Leu Leu Ala Glu Met Ser Asp His Thr Gly Phe Asp Phe Tyr Ala
305                 310                 315                 320

Gln Asp Pro Asn Leu Lys Met Thr Gln Ala Ala Ile Pro Asp Phe Gly
                325                 330                 335

Ala Gly Ala Met Glu Asn Trp Gly Leu Leu Thr Tyr Arg Glu Ala Tyr
                340                 345                 350

Leu Leu Tyr Asp Glu Gln His Thr Asn Ser Tyr Phe Lys Gln Ile Ile
            355                 360                 365

Ala Tyr Ile Leu Ser His Glu Ile Ala His Met Trp Phe Gly Asn Leu
        370                 375                 380

Val Thr Asn Ala Trp Trp Asp Val Leu Trp Leu Asn Glu Gly Phe Ala
385                 390                 395                 400

Arg Tyr Tyr Gln Tyr Phe Leu Thr Ala Trp Val Glu Asp Leu Gly Leu
                405                 410                 415

Ala Thr Arg Phe Ile Asn Glu Gln Val His Ala Ser Leu Leu Ser Asp
                420                 425                 430

Ser Ser Ile Tyr Ala His Pro Leu Thr Asn Pro Gly Val Gly Ser Pro
            435                 440                 445

Ala Ala Val Ser Ala Met Phe Ser Thr Val Thr Tyr Asn Lys Gly Ala
        450                 455                 460

Ser Ile Ile Arg Met Thr Glu His Leu Leu Gly Phe Asp Val His Arg
465                 470                 475                 480

Thr Gly Leu Arg Asn Tyr Leu Lys Asp Leu Ala Tyr Lys Thr Ala Gln
                485                 490                 495

Pro Ile Asp Leu Phe Thr Ala Leu Glu Ser Ala Gly Asn Gln Ala Gly
                500                 505                 510

Ala Leu Ser Ala Tyr Gly Ser Asp Phe Asp Phe Val Lys Tyr Tyr Glu
        515                 520                 525

Ser Trp Thr Glu Gln Pro Gly His Pro Val Leu Asn Val Gln Ile Asn
        530                 535                 540

His Gln Thr Gly Gln Met Thr Ile Thr Gln Arg Arg Phe Asp Ile Asp
545                 550                 555                 560

Thr Gly His Ser Val Gln Asn Arg Asn Tyr Ile Ile Pro Ile Thr Phe
                565                 570                 575

Thr Thr Gly Ala Asn Pro Ser Phe Asp Asn Thr Lys Pro Ser His Ile
                580                 585                 590

Ile Ser Lys Gly Val Thr Val Ile Asp Arg Gly Val Val Gly Asp Tyr
            595                 600                 605

Trp Thr Ile Phe Asn Ile Gln Gln Thr Gly Phe Tyr Arg Val Asn Tyr
        610                 615                 620

Asp Asp Tyr Thr Trp Asn Leu Ile Val Leu Ala Leu Arg Gly Ala Asp
625                 630                 635                 640

Arg Glu Lys Ile His Glu Tyr Asn Arg Ala Gln Ile Val Asn Asp Val
                645                 650                 655

Phe Gln Phe Ala Arg Ser Gly Leu Met Thr Tyr Gln Arg Ala Leu Asn
                660                 665                 670
```

```
Ile Leu Ser Phe Leu Glu Phe Glu Thr Glu Tyr Ala Pro Trp Val Ala
            675                 680                 685

Ala Ile Thr Gly Phe Asn Trp Leu Arg Asn Arg Leu Val Gly Lys Pro
        690                 695                 700

Gln Leu Asp Glu Leu Asn Glu Lys Ile Val Gln Trp Ser Ser Lys Val
705                 710                 715                 720

Met Gly Glu Leu Thr Tyr Met Pro Thr Glu Gly Glu Pro Phe Met Arg
                725                 730                 735

Ser Tyr Leu Arg Trp Gln Leu Ala Pro Val Met Cys Asn Leu Asn Val
            740                 745                 750

Pro Ala Cys Arg Ala Gly Ala Arg Ala Ile Phe Glu Asp Leu Arg Val
            755                 760                 765

Phe Gly His Glu Val Pro Val Asp Ser Arg Asn Trp Val Tyr Cys Asn
        770                 775                 780

Ala Leu Arg Asp Gly Gly Ala Gln Glu Phe Asn Phe Leu Tyr Asn Arg
785                 790                 795                 800

Phe Lys Ser His Asn Val Tyr Thr Glu Lys Ile Val Leu Leu Gln Thr
                805                 810                 815

Leu Gly Cys Thr Ser His Val Glu Ser Leu Asn Thr Leu Leu Thr Asp
            820                 825                 830

Ile Val Thr Pro Asn Gln Met Ile Arg Pro Gln Asp Tyr Thr Thr Ala
            835                 840                 845

Phe Asn Thr Ala Val Ser Gly Asn Glu Val Asn Thr Arg Leu Val Trp
        850                 855                 860

Asn Tyr Ile Gln Ala Asn Leu Gln Leu Val Phe Asn Ala Phe Ala Ser
865                 870                 875                 880

Pro Arg Thr Pro Leu Ser Tyr Ile Ala Ala Arg Leu Arg Thr Val Glu
                885                 890                 895

Glu Val Val Glu Tyr Gln Thr Trp Leu Asn Thr Thr Ala Ile Gln Ser
            900                 905                 910

Ala Leu Gly Thr Asn Tyr Asn Ala Ile Tyr Gly Asp Ser Val Ala Thr
            915                 920                 925

Tyr Asn Ser Ile Leu Trp Val Ser Thr Ile Glu Asp Ser Leu Ser Thr
930                 935                 940

Tyr Leu Thr Asn Gly Asn Asp Val Ile Glu Pro Ser Thr Ser Thr Thr
945                 950                 955                 960

Ser Thr Thr Ala Ala Pro Thr Thr Val Thr Gln Pro Thr Ile Thr Glu
                965                 970                 975

Pro Ser Thr Pro Thr Leu Pro Glu Leu Thr Asp Ser Ala Met Thr Ser
            980                 985                 990

Phe Ala Ser Leu Phe Ile Ile Ser  Leu Gly Ala Ile Leu  His Leu Ile
            995                 1000                 1005

Leu

<210> SEQ ID NO 14
<211> LENGTH: 39
<212> TYPE: DNA
<213> ORGANISM: Manduca sexta

<400> SEQUENCE: 14
ggaagatctt ccactgcatg cgtaactagt gcactcaac                                    39

<210> SEQ ID NO 15
<211> LENGTH: 50
<212> TYPE: DNA
```

```
<213> ORGANISM: Manduca sexta

<400> SEQUENCE: 15
gggatcccgt ccccgcgggg actcgatttg aaaaacaaat gaccatcatc          50
```

METHODS AND MATERIALS FOR IDENTIFYING NOVEL PESTICIDE AGENTS

CROSS-REFERENCE TO A RELATED APPLICATION

This application claims the benefit of U.S. Provisional Application Ser. No. 60/153,116, filed Sep. 7, 1999.

BACKGROUND OF THE INVENTION

Aminopeptidase N (APN) is an exopeptidase that hydrolyses neutral amino acids from the amino (N)-termini of different proteins. In different cell types, APN is expressed as a soluble cytoplasmic enzyme and a membrane-bound ectoenzyme. This enzyme is found on the surface of diverse cell types including lung, kidney, intestine and brain cells of many animals (Kenny et al., 1987). The ectoenzyme form is attached to epithelial cells of intestinal brush borders and respiratory tracts of vertebrates by a hydrophobic N-terminal stalk (Kenny et al., 1987 and Takasaki et al., 1991). In insects, however, ectoenzyme attachment is via a glycosyl-phosphatidylinositol (GPI) anchor (Tomita et al., 1994; Garczynski and Adang, 1995; Luo et al., 1996a; Luo et al., 1996b; Luo et al., 1997a; and Luo et al., 1 997b). GPI-anchored proteins are relatively mobile on the membrane surface and can be clustered in microdomains with other proteins and specific lipids. The base of the GPI-anchor interacts with the intracellular environment and has been implicated in physiological functions, intracellular sorting and transmembrane signaling (McConville and Ferguson, 1993).

In intestinal epithelial cells, APN is important for the final hydrolysis step of ingested proteins. APN also has several important physiological roles in other tissues. For example, APN is implicated in tumor cell invasion and inhibition of aminopeptidase activity can suppress tumor cell spread (Fujii et al., 1995). In brain cells, APN serves a role in the breakdown and inactivation of peptide neurotransmitters (Kenny et al., 1987). In bovine renal brush border membrane vesicles (BBMV), partially purified APN was found to be associated with a $Na^+$-dependent amino acid co-transporter (Plakidou-dymock et al., 1993).

APN molecules function as adventitious receptors for viruses. Human, feline, canine, and porcine coronaviruses utilize APN as their cellular receptors (Delmas et al., 1992; Yeager et al., 1992; and Tresnan et al., 1996). Cells refractory to coronaviruses from a particular animal species can be made susceptible by expression of an APN cDNA from that species (Benbacer et al., 1997). Human APN was shown to mediate human cytomegalovirus infection by increasing virus binding (McLaughlin and Aderem, 1995). Human, porcine and feline APNs have been cloned and expressed in different cell lines (Delmas et al.,. 1992; Yeager et al., 1992; Kolb et al., 1996; and Tresnan et al., 1996). Each of these vertebrate APNs were expressed on the cell surface as the N-terminal stalked form and bound a coronavirus.

Isoforms of APN located in the epithelial cells of insect midguts bind specifically to *Bacillus thuringiensis* Cry1 δ-endotoxins. Toxin-binding APNs are reported for several lepidopteran species (see, e.g., Knight et al., 1994; Sangadala et al., 1994; Gill et al., 1995; Valaitis et al., 1995; Luo et al., 1996; and Yaoi et al., 1997). For example, Cry1Aa, Cry1Ab and Cry1Ac, but not Cry1C or Cry1E toxins bind to a purified 115 kDa APN from *Manduca sexta* (Masson et al., 1995). Also partially purified preparations of APN catalyze toxin-induced pore formation in membrane vesicles (Sangadala et al., 1994) and planar lipid bilayers (Schwartz et al., 1997).

Several APN isoforms have been purified and cloned from different insect species (see, e.g., Knight et al., 1995; Gill et al., 1995; Valaitis et a, 1995; Luo et al., 1996; Yaoi et al., 1997; Denolf et al., 1997; and Hua et al., 1998). However, there has been limited success in expressing insect APN cDNA in insect cells. The only example to date involved the expression of *Plutella xylostella* 105 kDa APN in Sf9 cells using a baculovirus vector (Denolf et al., 1997). While the transformed cells of this study produced APN localized to the cell membrane, the APN was unable to bind to *B. thuringiensis* Cry1A toxins. Further, Denolf et al were unsuccessful in expressing two 120 kDa APNs from *Manduca sexta* using the same vector.

The complete structural and functional characterization of insect APN will require the successful expression of insect APN in insect cells. Successful expression of insect APN in insect cells as described in Luo et al. (1999) would also facilitate study of APN-toxin interactions, as well as provide a screening system for obtaining novel pesticide agents.

BRIEF SUMMARY OF THE INVENTION

The subject invention pertains to cells expressing a polynucleotide encoding an Aminopeptide N (APN), and methods of using the same to identify pesticide agents. One aspect of the invention pertains to an isolated polynucleotide which encodes a full length APN from *Manduca sexta* (M sexta) (SEQ ID NO: 1). Another aspect pertains to a fragment of said fill length polynucleotide which is sufficient to encode a functional protein.

In another aspect, the subject invention pertains to a cell or cells transfected with a polynucleotide encoding an APN or fragments thereof, such that a functional polynucleotide is expressed. Preferably, the polynucleotide is expressed forming a protein which is localized at the cell membrane of said cell or cells. A further aspect pertains to descendent generations of said cells which express APN that is localized on the cell membrane.

In a further aspect, the subject invention is directed to a method of identifying pesticide agents comprising obtaining a cell or cells transfected with a polynucleotide encoding an APN or fragments thereof, such that said polynucleotide is expressed to produce a protein localized at the cell membrane of said cell or cells, and screening one or more pesticide agents for their ability to produce an observable effect on said cell or cells.

In yet another aspect, the subject invention is drawn to novel pesticide agents obtained according to the subject methods.

In a still further aspect, the subject invention is drawn to an expression vector comprising a polynucleotide encoding APN or a functional fragment thereof.

An alternative aspect of the subject invention pertains to a method of identifying novel aminopeptidase inhibitors comprising obtaining cells having APN localized on the cell membranes thereof; and screening one or more compounds of interest for their ability to inhibit aminopeptidase activity.

BRIEF DESCRIPTION OF THE DRAWINGS

FIGS. 2A–2E represents the amino acid/polynucleotide sequence of the APN1a from M. sexta (SEQ ID NO: 1 and SEQ ID NO: 2, respectively).

FIG. 3 represents a comparison of the cloned *Manduca Sexta* 120 kDa APN1a (*M. sexta* 1a)(SEQ ID NO: 1)

with *M. sexta* 120 kDa APN2 (*M. sexta* 2)[Denolf et al. 1997](SEQ ID NO: 9), *Plutella xylostella* APN (*P. xylostella*)[Denolf et al. 1997](SEQ ID NO: 10), *M. sexta* 120 kDa APN1 (*M. sexta* 1)[Knight et al. 1995] (SEQ ID NO: 11), *Bombyx mori* APN (B. mori)[Hua et al. 1998](SEQ ID NO: 12), and *Heliothis virescens* APN (H. virescens) [Gill et al. 1995](SEQ ID NO: 13).

FIG. 4 represents immunoblot analysis of *M sexta* 120 kDa APN expressed in Sf21 cells and 115 kDa APN purified from *M sexta* midguts.

FIG. 5 represents autoradiograph of in vitro transcription and translation using various plasmid DNAs.

FIGS. 6A–6B represents optimization of expression of *M sexta* 120 kDa APN in Sf21

Figures 7A, 7B:
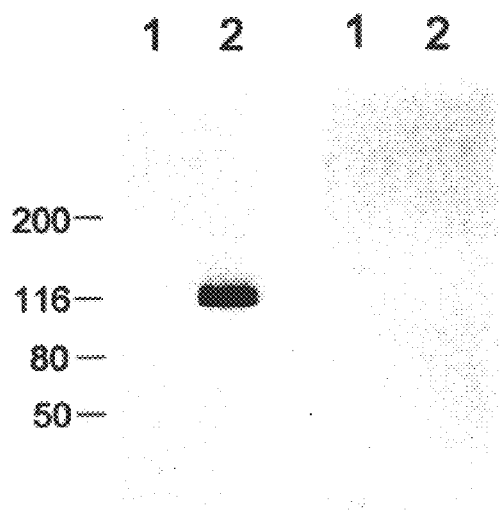

FIGS. 7A–7B represents immunoblot analysis of *M sexta* 120 kDa APN using anti-CRD antiserium.

FIGS. 8A–8D represents immunofluorescence localization of *M sexta* 120 kDa APN1a in Sf21 cells by confocal microscopy.

Figure 9:
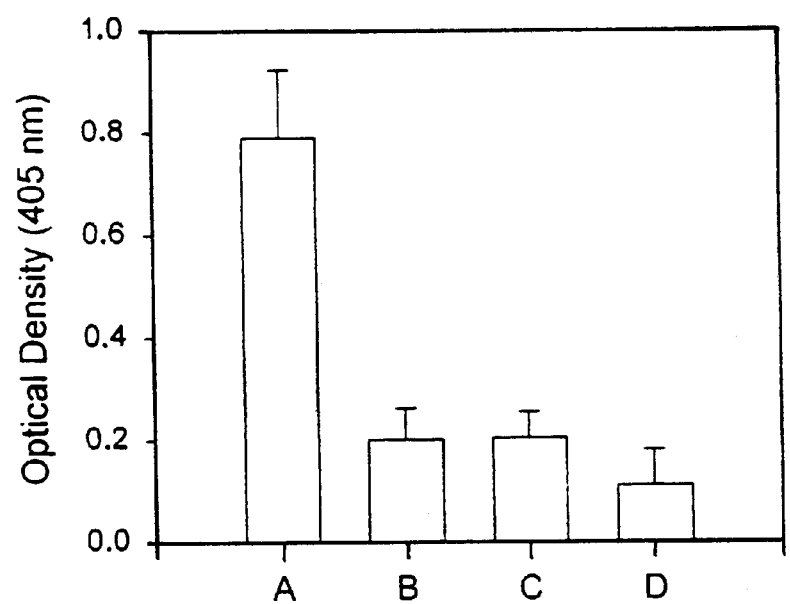

FIG. 9 shows APN activity of Sf21 cells transfected with pHSP120 (columns A and B) or pHSP-HR5 (columns C and D).

FIGS. 10A–10D represents immunofluorescence analyses of the binding of Cry1Ac toxin and anti-APN antibody to Sf21 cell surface by confocal microscopy.

FIGS. 11A–11D represents immunofluorescence analyses of the binding of Cry1Ba toxin 55 kDa form) and anti-APN antibody to Sf21 cell surface by confocal microscopy.

FIGS. 12A–12D represents immunofluorescence analyses of the binding of Cry1Ba toxin (65 kDa form) and anti-APN antibody to Sf21 cell surface by confocal microscopy.

Figure 13:

FIG. 13 represents immunoblot analysis of Cry1Ac, Cry1Ba and Cry3 toxin-affinity column purified *M sexta* 120 kDa APN from Sf21 cells and from *M sexta* midguts.

Figure 14:
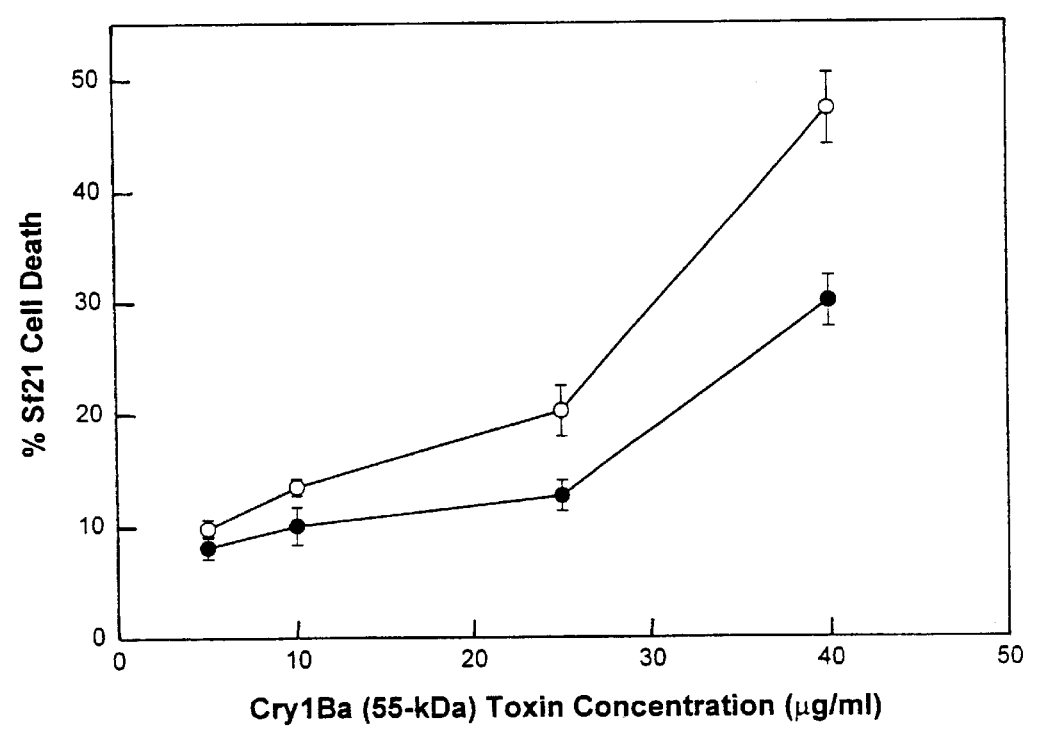

FIG. 14 represents cytotoxicity of Cry1Ba (55 kDa form) to Sf21 cells transfected with pHSP120 (open circle) and pHSP-HR5 (closed circle).

BRIEF DESCRIPTION OF THE SEQUENCES

SEQ ID NO: 1) is the amino acid sequence for the APN1a from *M. sexta*.

SEQ ID NO: 2) is the nucleotide sequence for the APN1a from *M. sexta*.

SEQ ID NO: 3) is the nucleotide sequence for PCR primer MS1.

SEQ ID NO: 4) is the nucleotide sequence for PCR primer MS1R.

SEQ ID NO: 5) is the nucleotide sequence for PCR primer MS5R.

SEQ ID NO: 6) is the nucleotide sequence for PCR primer MS4.

SEQ ID NO: 7) is the nucleotide sequence for vector primer T3.

SEQ ID NO: 8) is the nucleotide sequence for vector primer T7.

SEQ ID NO: 9) is the nucleotide sequence for the *M. sexta* 120 Kda APN2 (Denolf et al. 1997).

SEQ ID NO: 10) is the nucleotide sequence for the *P. xylostella* APN (Denolf et al. 1997).

SEQ ID NO: 11) is the nucleotide sequence for the *M. sexta* 120 kDa APN1 (Knight et al. 1995).

SEQ ID NO: 12) is the nucleotide sequence for the *B. mori* APN (Hua et al. 1998).

SEQ ID NO: 13) is the nucleotide sequence for the *H. virescens* APN (Gill et al. 1995).

SEQ ID NO: 14) is the nucleotide sequence for the PCR primer 5'-pAHR5.

SEQ ID NO: 15) is the nucleotide sequence for PCR primer 3'-pAHR5.

DETAILED DISCLOSURE OF THE INVENTION

As noted above, the subject invention relates to a cell or cells transfected with a polynucleotide encoding an APN protein, or fragment thereof, and methods using the subject cells for identifying novel pesticide agents. The subject invention provides, for the first time, insect cells that express a B.t. toxin binding aminopeptidase localized at their cell membrane. Further, the subject invention is the first demonstration of cultured cells which express a protein capable of binding to a toxin. Further, binding to the toxin is capable of producing an observable effect on such cells, including effecting the death of such cells.

In one embodiment, the subject invention is drawn to a polynucleotide that encodes an APN from *M. sexta*. In a preferred embodiment, the polynucleotide of the subject invention comprises a nucleotide sequence as shown in FIGS. 2A–2E (SEQ ID NO: 2).

In another embodiment, the subject invention is drawn to a cell or cells transfected with a polynucleotide molecule that comprises a nucleotide sequence encoding an APN protein or fragment thereof, wherein said APN protein or fragment thereof is localized at the cell membrane of said cell or cells. Further, the APN protein or fragment thereof is preferably, but not necessarily, anchored to said cell membrane by at least one glycosyl-phosphatidyl inositol anchor. In a preferred embodiment, said APN protein or fragment thereof which is localized at the cell membrane is capable of binding a toxin. In a more preferred embodiment, said APN protein or fragment thereof mediates an observable toxicity to said cell or cells, including death upon contacting a toxin.

The term "transfection" as used herein means an introduction of a foreign DNA or RNA into a cell by mechanical inoculation, electroporation, agroinfection, particle bombardment, microinjection, or by other known methods.

The term "transformation" as used herein means a stable incorporation of a foreign DNA or RNA into the cell which results in a permanent, heritable alteration in the cell. Accordingly, the skilled artisan would understand that transfection of a cell may result in the transformation of that cell.

As described in the background of the invention, many Bt toxins have been isolated and sequenced. Polynucleotides encoding any known Bt toxins or those yet to be discovered and active fragments thereof (see, for example, U.S. Pat. No. 5,710,020) can be used in accord with the teachings herein. These include, but are not limited to, polynucleotides encoding Cry1Aa, Cry1Ab, Cry1Ac, Cry1B, Cry1C, Cry1E, and Cry3A. See Crickmore et al. (1998) for a description of other Bt toxins.

As used hereinafter, "APN" includes full-length APN and fragments of APN operable for the uses disclosed herein.

In order to provide an understanding of a number of terms used in the specification and claims herein, the following definitions are provided.

An isolated nucleic acid or polynucleotide is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, and (ii) cell clones, e.g., as these occur in a DNA library such as a cDNA or genomic DNA library.

A nucleotide sequence is operably linked when it is placed into a functional relationship with another nucleotide sequence. For instance, a promoter is operably linked. to a coding sequence if the promoter effects its transcription or expression. Generally, operably linked means that the sequences being linked are continguous and, where necessary to join two protein coding regions, contiguous and in reading frame. However, it is well known that certain genetic elements, such as enhancers, may be operably linked even at a distance, i.e., even if not contiguous.

Polynucleotide probes include an isolated polynucleotide attached to a label or reporter molecule and may be used to identify and isolate other APN-encoding polynucleotides. Probes comprising synthetic oligonucleotides or other polynucleotides may be derived from naturally occurring or recombinant single or double stranded nucleic acids or be chemically synthesized. Polynucleotide probes may be labelled by any of the methods known in the art, e.g., random hexamer labeling, nick translation, or the Klenow fill-in reaction.

The polynucleotides may also be produced by chemical synthesis, e.g., by the phosphoramidite method described by Beaucage and Caruthers (1981) *Tetra. Letts.*, 22:1859–1862 or the triester method according to Matteuci et al. 91981) *J. Am. Chem. Soc.*, 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typically selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

It will be recognized by those skilled in the art that the DNA sequences may vary due to the degeneracy of the genetic code and codon usage. All DNA sequences which code for the APN are included in this invention, including DNA sequences as given in SEQ ED NO: 2 having an ATG preceding the coding region for the mature protein.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified APN sequence can be used to identify and isolate additional, nonexemplified nucleotide sequences which will encode functional equivalents to the sequences given in SEQ ID NO: 2, or an amino acid sequence of greater than 90% identity thereto and having equivalent biological activity. DNA sequences having at least 90, or at least 95% identity to the recited DNA sequences of SEQ ID NO: 2 and encoding functioning APN are considered equivalent to the sequences of SEQ ID NO: 2 and are included in the definition of an APN encoding sequence. Following the teachings herein and using knowledge and techniques well known in the art, the skilled worker will be able to make a large number of operative embodiments having equivalent DNA sequences to those listed herein without the expense of undue experimentation. sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul et al (1990) *J. Mol. Biol.* 215:402–410. BLAST nucleotide searches are performed with the NBLAST program, score =100, wordlength =12, to obtain nucleotide sequences with the desired percent sequence identity. To obtain gapped alignments for comparison purposes, Gapped BLAST is used as described in Altschul et al. (1997) Nucl. Acids. Res. 25:3389–3402. When utilizing BLAST and Gapped BLAST programs, the default parameters of the respective programs (NBLAST and XBLAST) are used. See http://www.ncbi.nih.gov.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987)*DNA Probes*, Stockton Press, New York, N.Y., pp. 169–170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with 32P-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula from Beltz et al. (1983).

$$Tm=81.5° C.+16.6 \log [Na+]+0.41(\%G+C)-0.61 (\%formamide)$$
$$600/\text{length of duplex in base pairs.}$$

Washes are typically carried out as follows:
(1) Twice at room temperature for 15 minutes in 1×SSPE, 0.1% SDS (low stringency wash).
(2) Once at Tm-20° C. for 15 minutes in 0.2×SSPE, 0.1% SDS (moderate stringency wash).

For oligonucleotide probes, hybridization was carried out overnight at 10–20° C.
below the melting temperature (Tm) of the hybrid in 6×SSPE, 5×Denhardt's solution, 0.1% SDS, 0.1 mg/ml denatured DNA. Tm for oligonucleotide probes was determined by the following formula from Suggs et al. (1981):

$$Tm (° C.)=2 \text{ (number T/A base pairs)}+4\text{(number G/C base pairs)}$$

Washes were typically carried out as follows:
(1) Twice at room temperature for 15 minutes 1×SSPE, 0.1% SDS (low stringency wash).
(2) Once at the hybridization temperature for 15 minutes in 1×SSPE, 0.1%
SDS (moderate stringency wash)

In general, salt and/or temperature can be altered to change stringency. With a labeled DNA fragment of greater than about 70 or so bases in length, the following can be used:

Low: 1 or 2×SSPE, room temperature
Low: 1 or2×SSPE, 42° C.
Moderate: 0.2×or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide sequences of the invention can be used in the same manner as the exemplified polynucleotide sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage.

In a further embodiment, the subject invention provides expression vectors comprising one or more polynucleotides comprising nucleotide sequences encoding APN and capable of expressing APN in a suitable host cell. In the vectors of the subject invention, the polynucleotide encoding APN is operably linked to suitable transcriptional and/or translational regulatory elements to effect expression of the APN in a suitable host cell. The regulatory elements may be derived from mammalian, microbial, viral or insect genes and include, for example, promoters, enhancers, transcription and translation initiation sequences, termination sequences, origins of replication, and leader and transport sequences. Suitable regulatory elements are selected for optimal expression in a desired host cell.

Possible regulatory sequences can include, but are not limited to, any promoter already shown to be constitutive for expression, such as those of viral origin (e.g., IEI promoter from Baculoviruses) or so-called "housekeeping" genes (ubiquitin, actin, tubulin) with their corresponding termination/poly A +sequences. In addition, the gene can be placed under the regulation of inducible promoters and their termination sequences so that gene expression is induced by light (rbcS-3A, cab-1), heat (hsp gene promoters) or wounding (mannopine, HGPGs). Other suitable promoters include the metallothionein promoter, dexamethasone promoter, alcohol dehydrogenase promoter, and the baculovirus promoters, i.e., the early promoter (e.g., IE-1 and et1), the late promoters (e.g., vp39 and p6.9), the very late promoters (e.g., po1h and p10) and the hybrid promoter (e.g., vp39/po1h).

It is clear to one skilled in the art that a promoter may be used either in native or truncated form, and may be paired with its own or a heterologous termination/polyA +sequence. In a preferred embodiment, the subject vectors are regulated by *D. melanogaster* HSP70 promoter.

Expression vectors can be constructed by well known molecular biological methods as described for example in Sambrook et al. (1989), or any of a myriad of laboratory manuals on recombinant DNA technology that are widely available. Expression vectors into which the polynucleotides of the present invention can be cloned under the control of a suitable promoter are also commercially available. Recombinant viral vectors, including retroviral, baculoviral, parvoviral and densoviral vectors can be used but are not particularly preferred. In host cells containing vectors having an inducible promoter controlling the expression of the nucleic acid encoding APN, expression is induced by methods known in the art and suitable for the selected promoter. For example, expression of nucleic acids under the control of the metallothionein promoter is induced by adding cadmium chloride or copper sulfate to the growth media of host cells.

In a specific embodiment, the subject invention provides a host cell containing a vector comprising nucleotide sequences encoding APN under the control of a promoter. The host cell may be procaryotic or eukaryotic, including bacterial, yeast, insect and mammalian cells. Insect and mammalian cells are preferred. Particularly preferred host cells include insect cell lines, such as, for example, *Spodoptera frugiperda* (Sf9 and Sf21) and *Trichoplusia ni* (Tn cells), *Estigma acrae* (Ea4 cells), *Drosophila melanogaster* (Dm cells), *Choristoneura fumiferama* (Cf-y cells), *Mamestra brassicae* (MaBr-3 cells), *Bombyx mori* (MnN-4 cells), *Helicoverpa zea* (Hzlb3 cells), and *Lymantria dispar* (Ld652Y cells), among others. The host cells. may be transformed, transfected or infected with the expression vectors of the present invention by methods well-known to those of ordinary skill in the art. Transfection may be accomplished by known methods, such as liposome mediated transfection, calcium phosphate mediated transfection, microinjection and electroporation.

Cells of the subject invention may be transfected with a polynucleotide comprising a nucleotide sequence of FIGS. 2A–2E (SEQ ID NO: 2), or fragment thereof. One skilled in the art would readily appreciate that polynucleotides encoding other APNs may be substituted for FIGS. 2A–2E (SEQ ID NO: 2). Examples of toxin binding APNs have been reported for several species (see, e.g., Knight et al., 1994; Sangadala et al., 1994; Gill et al., 1995; Luo et al., 1996; Yaoi et al., 1997; Denolf et al., 1997; and Huo et al., 1998 incorporated herein by this reference). Equipped with the teachings herein, the skilled artisan would be able to transfect insect cells with these, as well as future isolated APN-encoding polynucleotides, to produce APN expressing cells.

The skilled artisan will note that polynucleotides preferred for practicing the subject invention encode proteins capable of expression in cells, localization to cell membrane, and toxin binding. Accordingly, fragments of APN sequences as well as functional mutants may equally be used in practicing the subject invention. Such fragments and mutants will be readily obtainable following the teachings herein coupled with the state of the art. For example, using specifically exemplified polynucleotides as probes, useful polynucleotides can be obtained under conditions of appropriate stringency. Standard hybridization conditions include hybridization with nonspecific DNA, such as salmon DNA, at 50° C. and washing at 45° C. To obtain polynucleotides having the lowest detectable homology with exemplified APNs, hybridization is conducted under conditions of low standard stringency (30–37° C. and 4–6×SSC). More closely related APN-like polynucleotides can be obtained under moderate standard stringency conditions (40–50° C. in 1×SSC).

In a further embodiment, the subject invention is directed to a method of identifying novel pesticide agents comprising the steps of obtaining cells transfected with one or more of the polynucleotides encoding APNs, whereby said polynucleotides are expressed to produce at least one protein that is localized at the cell membrane of said cells; and screening one or more pesticide agents for their ability to produce an observable effect on said cells. The observable effect may be related to a change in metabolism or morphology. The effect may be cytotoxic which may manifest itself, for example, as reduced thymidine uptake, slower increase in optical density of the culture, reduced exclusion of vital dyes (e.g., trypan blue), increased release of viability markers such as chromium and rubidium and the like. The differential response between the pesticide-treated cells and the cells absent the pesticide may be qualitatively or quantitatively noted. Further, the strength of the pesticide can be assessed by noting the strength of the response. While the subject invention is useful for screening a variety of pesticide agents, one skilled in the art will appreciate that the subject methods are particularly useful in identifying novel natural or mutated B. t. toxins.

In a further embodiment, the subject invention is directed to novel pesticide agents obtained by the subject screening methods.

In yet another embodiment, the subject invention is drawn to a method of identifying novel APN inhibitors comprising obtaining cells as described herein, and screening compounds of interest for their ability to inhibit aminopeptidase activity.

The teachings of all patents and publications cited throughout this specification are incorporated by reference in their entirety to the extent not inconsistent with the teachings herein.

Following are examples which illustrate procedures for practicing the invention. These examples should not be construed as limiting. All percentages are by weight and all solvent mixture proportions are by volume unless otherwise noted.

EXAMPLE 1

1.1. Cloning and Sequencing of *M. sexta* 120 kDa APN

A PCR strategy similar to that described in Tresnan et al. (1996) was used to clone the 120 kDa APN1a cDNA from *M. sexta*. Four PCR primers were designed from the published 120 kDa APN1 sequence (Knight et al., 1995):

MS1, 5'ATTTTCTTGGGGGTCGCCCTTC3' (SEQ ID NO: 3); MS1R, 5'ACGCTACCATGTTAATG3' (SEQ ID NO: 4); MS5R, 5'TGCTGTGTCATTCTGAG3' (SEQ ID NO: 5); MS4, 5'AGGAGATTCGCCCATGACGCC3' (SEQ ID NO: 6). Two vector primers were T3, 5'AATTAACCCTCACTAAAGGG3' (SEQ ID NO: 7) and T7, 5'GTAATACGACTCACTATAGGGC3' (SEQ ID NO: 8). Primers were synthesized by the Molecular Genetics Facility (University of Georgia). A midgut cDNA library from *M. sexta*constructed in ZAPII vector (Stratagene, La Jolla, Calif.) was kindly provided by Dr. R. Graf. (Zoologisches Institut der Universitat, Munich, Germany).

All PCR reagents were purchased from FisherBiotech (Pittsburgh, Pa.). PCR was performed as follows: 30 cycles of 55° C./2 min, 72° C./3 min, and 94° C./1 min. A sample of the phage stock from cDNA library (5 μl, titer: $1\times10^6$ pfu/μl) was heated at 100° C. for 5 min, and then used as a template. Primers MS1 and MS1R, corresponding to sequences of the 5' and 3' ends of the APN cDNA amplified a 3 kb product. Primers MS5R and T3 gave a 1.4 kb PCR product. The 3 kb and 1.4 kb PCR products were each cloned into pGEM-T (Promega, Madison, Wis.) and called pGEM6 and pGEM4.5, respectively. The plasmid p120 was constructed by the ligation of a 0.4 kb NotI/EcoRV fragment of pGEM4.5 into the same sites of pGEM6. The third primer pair, MS4 and T7, was used to amplify the 3' end of APN from the cDNA library. The resulting 2 kb PCR product was digested with BglII and ApaI and separated on a low-melting temperature agarose gel. The desired fragment of about 0.4 kb was purified and cloned into the BglII/ApaI sites of p120 to give pAPN 120. The 3.2 kb insert of pAPN120 was completely sequenced in both strands using a ALF DNA Sequencer (Molecular Genetics Facility, University of Georgia).

1.2 Construction of Expression Plasmids, pET120-2, pET120-3 and pET1000.

The plasmid pET30A (Novagen, Madison, Wis.) was used to express recombinant APN in *E. coli*. For construction of pET120-2, the entire coding region of 120 kDa APN cDNA of *M sexta* (3.2 kb) was excised from pAPN120 with BamHI and XhoI, and then purified and cloned into pET30A digested with the same enzymes. The plasmid pET120-3 was constructed by inserting an EcoRV-XhoI fragment of pAPN120 into pET30A. The EcoRV-XhoI fragment of 120 kDa APN cDNA encodes a 5'-truncated 96 kDa protein. The plasmid pET1000 carrying the 5' and 3'-truncated form of APN (31 kDa) was constructed by the ligation of a 851 bp EcoRV-SacI fragment of 120 kDa APN cDNA into pET30A. These constructions were verified by restriction enzyme analyses or DNA sequencing.

1.3 In Vitro Transcription and Translation

In vitro transcription and translation were performed using the Single Tube Protein System 2 (STP2) (Novagen, Madison, Wis.) according to the manufacturer's instructions. Plasmids, pET120-2 and pET120-3, were transcribed at 30° C. for 15 min and then translated by adding 30 µl of STP2 translation mix and 4 µl of $^{35}$S-methionine. After incubation at 30° C. for 60 min, the reaction mixture (5 µl) was treated with 20 µl of Laemmli sample buffer. Laemmli (1970). The sample was heated at 90° C. for 5 min and then centrifuged at 12 000×g for 2 min. The supernatant was separated by SDS-10% polyacrylamide gel electrophoresis (SDS-PAGE). After electrophoresis, the gel was immersed in staining buffer for 10 min, rinsed briefly with water, and exposed to X-ray film at room temperature for 12h.

Results

Figure 3A:
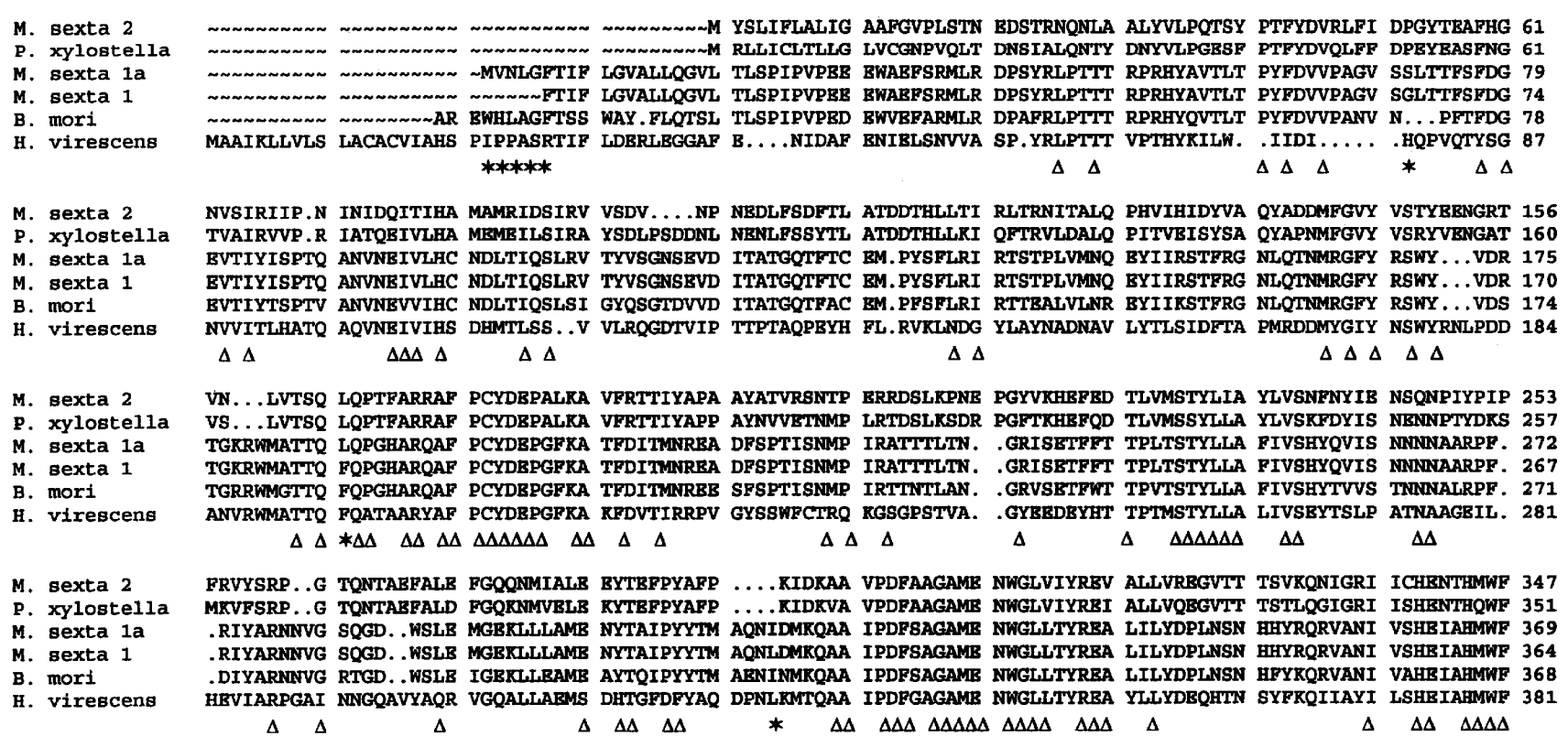
Figure 3B:
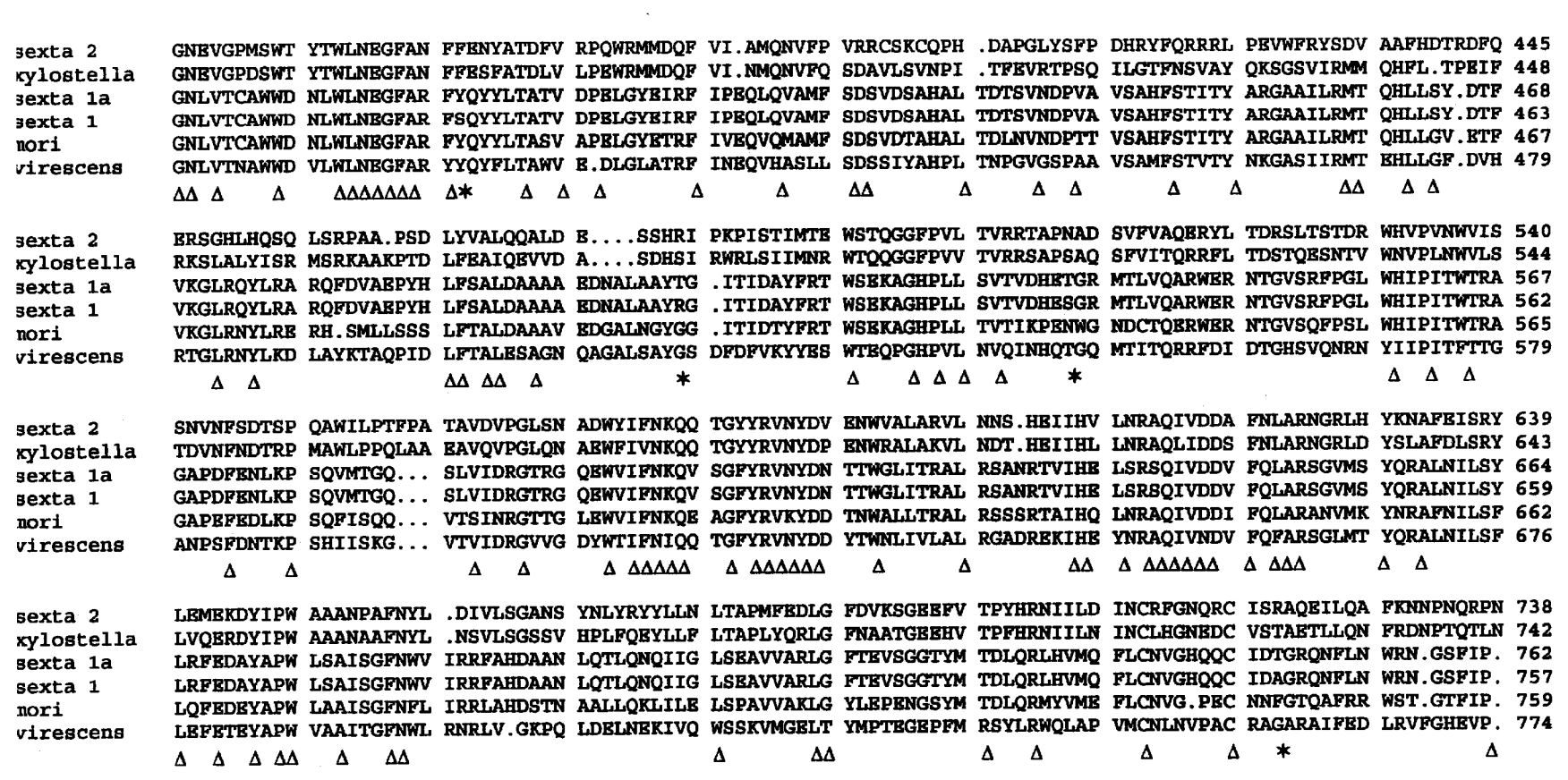
Figure 3C:
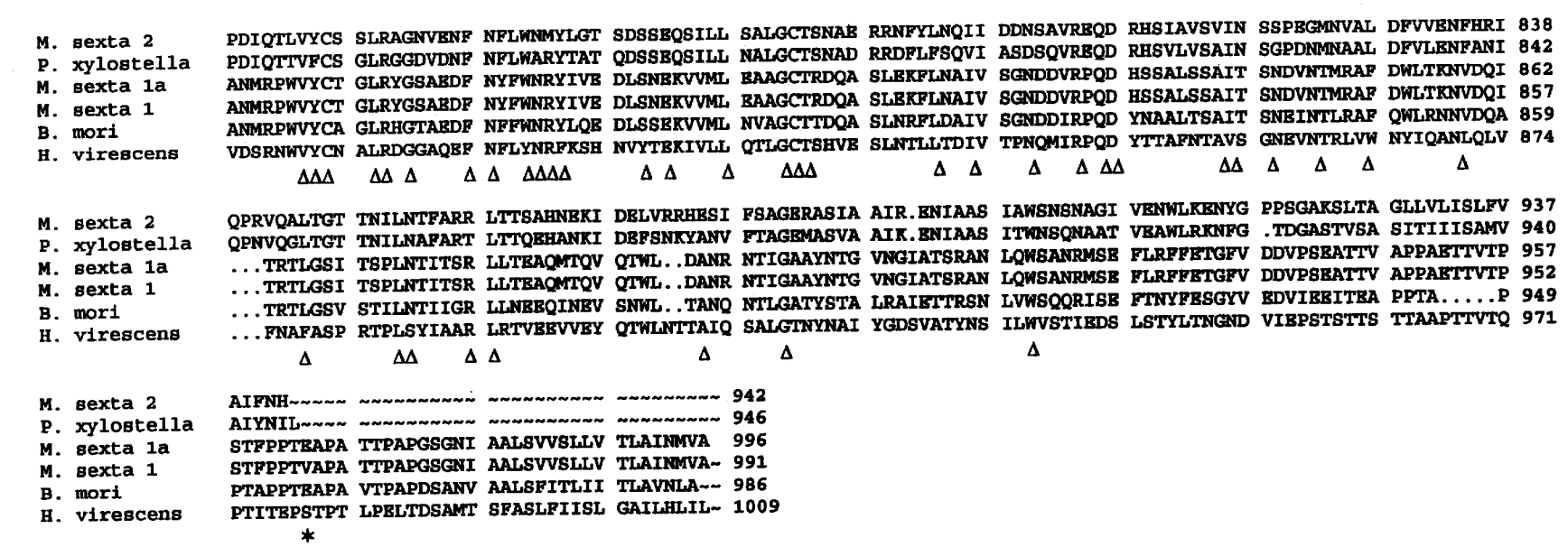

A *M. sexta* midgut cDNA library in λZAPII vector was used as a template for PCR amplification of full-length or partial cDNAs for the 120 kDa APN. Primers (MS1/MS2) corresponding to sequences from the 5' and 3' ends of the cloned *M. sexta* 120 kDa APN1 cDNA (Knight et al., 1995) gave the expected 3 kb product. A second primer (MS5) and vector primer (T3) amplified a 1.4 kb product, while the third pair of primers, MS4 and T7, produced a 2 kb fragment. DNA sequencing showed that the 5' and 3' ends of the 3 kb and 2 kb PCR fragments were identical to the published sequence of *M. sexta* 120 kDa APN1 (Knight et al., 1995). The 3' end of the 1.4 kb fragment had the expected APN nucleotide sequence, however the 5' end had an additional 30 nucleotides. A full-length cDNA clone, called pAPN120, was constructed from the overlapping PCR clones and completely sequenced from both DNA strands (FIGS. 2A–2E). Plasmid pAPN120 contains a 3164 bp insert with a 2985 bp open reading frame beginning with a consensus Kozak sequence (AGAATGG) at nucleotide 15. Kozak (1987). The open reading frame encodes a protein of 995 amino acids including additional 5 amino acids upstream of the reported *M. sexta* APN1 clone. Knight et al. (1995). A comparison of the amino acid sequences of our APN cDNA clone (APN1a) and APN1 showed that our clone has 8 amino acids different from the APN1 (FIG. 3). These different amino acids do not modify any putative glycosylation or GPI-anchorsites. Interestingly, some of these amino acids (for example, $L^{211}$, $I^{313}$, $Y^{422}$, $T^{568}$, $E^{1007}$) in our APN1a clone (SEQ ID NO: 1) are actually identical to, or share electrostatic properties or polarity with other cloned APNs (FIG. 3) (SEQ ID NOS: 9, 10, 1, 11, 12, and 13) disclosed, for example, in Knight et al. (1995) (SEQ ID NO: 11); Gill et al. (1995) (SEQ ID NO: 13); Denolf et al. (1997) (SEQ ID NOS: 9 and 10); and Hua et al. (1998) (SEQ ID NO: 12). In vitro transcription and translation of APN1a cDNA in a rabbit reticulocyte lysate system was done to establish the molecular size of non-glycosylated APN1a. Plasmid pET120-2 carrying full-length APN1a cDNA resulted in a protein of 110 kDa (FIG. 5, lane 3), while pET120-3 containing 5'-truncated APN1a cDNA gave a 96 kDa protein. (FIG. 5, lane 4). The control plasmid, pCITEβ-gal, containing the *E. coli* β-galactosidase gene yielded a 116 kDa protein (FIG. 5, lane 2). The molecular size of translated APN1a was the same as predicted from the deduced amino acid sequence, supporting the putative translation start site in our cDNA clone. Also, the determined 110 kDa size for non-glycosylated APN1a provided a reference size standard for comparison with APN in *M. sexta* BBMV and cultured insect cells.

EXAMPLE 2

2.1 Expression of the Recombinant APN in *E. coli* and Production of the Polyclonal Antibody To express truncated 31 kDa APN in *E. coli*, plasmid pET1000 was electroporated into an *E. coli* expression host, BL21 (DE3), and recombinant HIS-tagged APN expressed and purified according to the manufacturer's instructions (Novagen, Madison, Wis.) using a Histrap column (Pharmacia, Piscataway, N.J.). Eluted fractions containing expressed APN were pooled and successively dialyzed against 4 M, 2 M, 1 M and 0 M urea in 50 mM $Na_2CO_3$, pH 10. The resulting sample was then centrifuged at 27 000×g for 30 min. The pellet was suspended in 1 ml of PBS (phosphate-buffered saline), and the supernatant was concentrated to 1 ml. Protein concentration in the supernatant and pellet were about 0.5 and 0.8 mg/ml, respectively. Both samples were stored at −80° C. until use. Antisera against 31 kDa truncated APN was raised by immunization of a NZW (SPF) rabbit with 0.2 mg of truncated APN administered in complete Freud's adjuvants (Polyclonal Antibody Production Service, University of Georgia). The rabbit was boosted two times with truncated APN protein. The rabbit serum was collected 10 days after the second boost. Reactivity of the rabbit serum was assessed by Western blotting. IgG was purified using a ProteinA column and kit (Pierce, Rockford, Ill.).

2.2 Construction of the Expression Vector pHSP120

The plasmid pHSP70PL that contains the *Drosophila melanogaster* HSP70 promoter and the 5' untranslated leader of HSP70 is described in Morris and Miller (1992). We first constructed plasmid pHSP-HR5. This plasmid contains the polyadenylation sequence (poly A) from the p35 gene and half of the homologous region 5 (hr5) of *Autographa californica* nuclear polyhedrosis virus (AcMNPV), a sequence extending from nucleotide 17,344 to 17,636 (sequence according to Ayres et al., 1994). Two PCR primers (5'-pAHR5: 5'GGAAGATCTTCCACTGCAT-GCGTAACTAGTGCACTCAAC3' (SEQ ID NO: 14) and 3'-pAHR5:

5'GGGATCCCGTCCCCGCGGGGACTC-GATTTGAAAAACAAATGACCATCATC3' (SEQ ID NO: 15)) were designed to amplify the poly A and a part of the hr5 sequence from the plasmid pH1PQ which contains the Hind III Q restriction fragment of AcMNPV genomic DNA. The PCR product (316 bp)

was digested with BglII and BamHI, and then inserted into pHSP70PL vector treated with BglII. The resulting plasmid, pHSP-HR5, was verified by restriction enzyme analyses and DNA sequencing.

5' GGGATCCCGTCCCCGCGGGGACTC-GATTTGAAAAACAAATGACCATCATC3' (SEQ ID NO: 9)) were designed to amplify the poly A and a part of the hr5 sequence from the plasmid pH1PQ which contains the Hind III Q restriction fragment of AcMNPV genomic DNA. The PCR product (316 bp) was digested with BglII and BamHI, and then inserted into pHSP70PL vector treated with BglII. The resulting plasmid, pHSP-HR5, was verified by restriction enzyme analyses and DNA sequencing.

Figure 1:
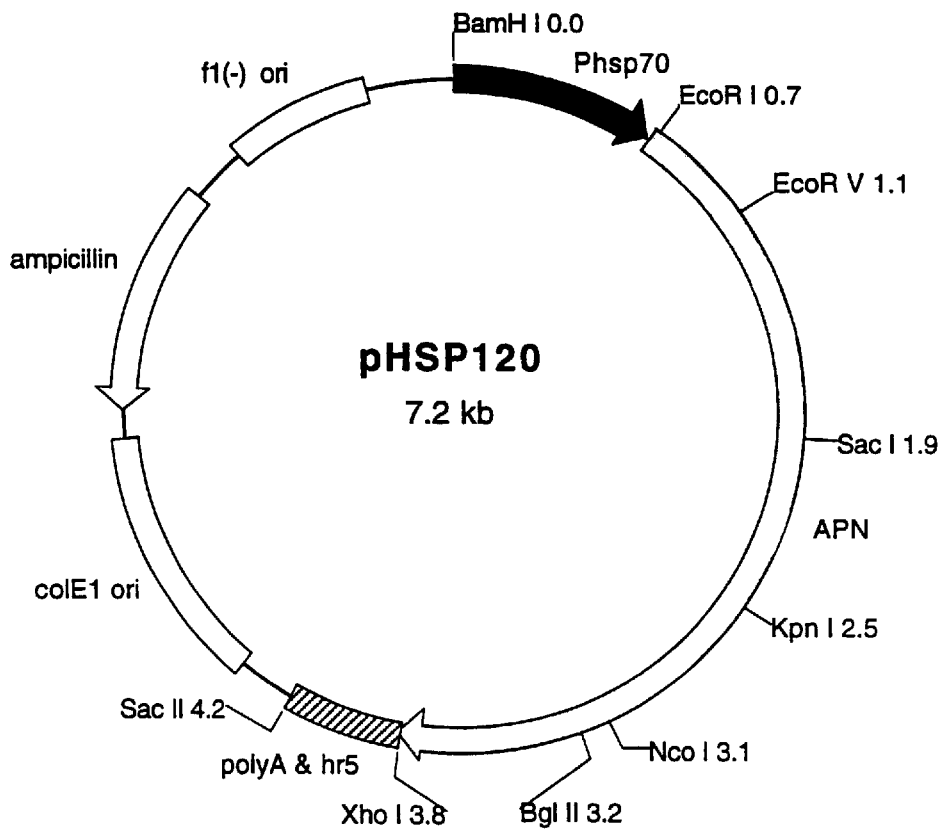
FIG. 1 represents construction of the expression vector pHSP120.

Plasmid pHSP120 was then constructed by inserting a 3.2 kb SphI/BamHI fragment of pAPN120 into pHSP-HR5. The detailed structure of pHSP120 is shown in FIG. 1.

2.3 Transfection and Expression of the 120 kDa APN in S21 Cells

The pHSP120 plasmid DNA was isolated and purified using a Plasmid Maxi Kit (Qiagen, Valencia, Calif.). Sf21 (IPLB-Sf21) cells (Vaughn et al., 1977) were plated at $1.8 \times 10^6$ cells per plate (60 mm diameter) prior to transfection with pHSP120 DNA. Plasmid DNA (10 µg) was mixed with 5 µl of Lipofectin reagent (Gibco BRL, Gaithersburg, Md.) and combined with 1 ml of TC-100 medium (Gibco BRL, Gaithersburg, Md.). The mixture was incubated at room temperature for 15 min. Following 3 washes with TC-100 medium, the DNA/Lipofectin mixture was added to the cells, and then the cells were incubated at room temperature for 4 h on a rocker. After removal of DNA/Lipofectin mixture, TC-100 with 10% fetal bovine serum (4 ml) was added to the plates and the cells were incubated at 27° C. overnight. Expression of 120 kDa APN in Sf21 cells was induced by heat-shocking cells at 42° C. for 30 min the following day. After incubation at 27° C. for 24 h, the cells were collected and analyzed using immunofluorescence localization and Western blotting.

2.4 Immunoblot Analysis

Non-heat-shocked or heat-shocked insect cells ($10^7$ cells) were lysed in 200 µl Laemmli sample buffer (Laemmli, 1970), and the sample was centrifuged at 12 000×g for 5 min. The supernatant (15 µl) was separated by 8% SDS-PAGE and electrophoretically transferred to nitrocellulose membrane (Millipore Corp., Bedford, Mass.) in transfer buffer (Towbin et al., 1979) at 4° C. overnight. The membrane was blocked with 5% non-fat dry milk in PBST at room temperature for 1 h, and then probed with anti-APN antibody (0.5 µg/ml) in PBST containing 0.1% non-fat dry milk for 2 h. After three washes with PBST, the membrane was incubated with horseradish peroxidase (HRP)-conjugated donkey anti-rabbit IgG (1:3000) (Amersham, Piscataway, N.J.) in PBST containing 0.1% non-fat dry milk at room temperature for 2 h. Protein bands were visualized with ECL Western Blotting Kit (Amersham, Piscataway, N.J.) according to manufacturer's instructions.

Results

The heat-shock expression vector pHSP120 containing M. sexta APN1a cDNA (FIG. 1) was transfected into Sf21 cells, following which the cells were heat-shocked and tested for the presence of APN. As shown in FIG. 4, anti-APN antibody specifically recognized the expressed APN (FIG. 4, lane 2), but not the proteins from Sf21 cells transfected with control vector (FIG. 4, lane 1). This anti-APN antibody also bound to 115 kDa APN purified from M. sexta midgut BBMV (FIG. 4, lane 3). The 115 kDa APN is the PIPLC-cleaved form of 120 kDa APN. Lu and Adang (1996). FIG. 6A shows a Western blot of Sf21 cells transfected with increasing amounts of plasmid pHSP120 DNA. Optimal expression of 120 kDa APN1a was achieved when 10 µg of DNA was used to transfect Sf21 cells (FIG. 6A). Optimal times for detecting expressed 120-kDa APN1a in Sf21 cells were between 12 h and 24 h after heat-shock (FIG. 6B). The molecular size of expressed APN1a was estimated to be 120 kDa, which is the same as that from M. sextaBBMV (FIG. 6A). Several closely migrating bands are visible in FIGS. 6A and B, suggesting that M sexta APN1a may be heterogeneously glycosylated in Sf21 cells.

EXAMPLE 3

3.1 PIPLC Digestion and GPI Anchor Detection

Sf21 cells ($10^7$ cells) were lysed in 200 µl Laemmli sample buffer (Laemmli, 1970), and 15 µl of supernatant prepared as described above, was separated by SDS-PAGE, and then electrophoretically transferred to nitrocellulose membrane (Millipore Corp., Bedfore, Mass.). The membrane was blocked with 50 mM Tris-HCl, pH 7.4, 150 mM NaCl, 1 mM EDTA, 0.05% Tween-20 (buffer A) containing 3% BSA at room temperature for 2 h. After three washes with buffer A, the membrane was treated with phosphatidylinositol-specific phospholipase C (PIPLC, Sigma) (1.5 U) overnight at room temperature in 10 ml of 20 mM Tris-HCl, pH 7.4, 0.1%Triton-X100, 1 mM DTT and 3% BSA. The presence of a cleaved GPI group was detected using a polyclonal antibody against the cross-reacting determinant (CRD) of GPI-anchored proteins as described previously (Garczynski and Adang, 1995) (anti-CRD serum was kindly provided by Dr. K. Mensa-Wilmot, University of Georgia). Protein bands were visualized with ECL Western blotting Kit (Amersharn, Piscataway, N.J.).

3.2 Preparation of BBMV and Purification of M. sexta 115 kDa APN

M. sexta larvae were reared on artificial diet (Southland Products, Inc.; Lake Village, Ark.) at 26° C., 70% relative humidity with a photoperiod of 12:12 (Light:Dark) h. Midguts were dissected from second day 5th instar larvae, and either immediately used to prepare brush border membrane vesicles (BBMV) or stored at −80° C. BBMV were prepared according to that described in Wolfersberger et al. (1987) as modified in Ferre et al. (1991) and stored in 0.3 M mannitol, 5 mM EGTA, 17 mM Tris-Cl, pH 7.5, at −80° C. until needed. The 115 kDa M. sexta APN was purified as described previously (Lu and Adang, 1996).

3.3 Immunofluorescence Localization

Sf21 cells were plated onto a microscope cover glass (18×18 mm) in a tissue culture dish (60×15 mm diameter), and then transfected and heat-shocked as described above. After three washes with Insect PBS (1 mM $Na_2HPO_4$, 10.5 mM $KH_2PO_4$, 140 mM NaCl, 40 mM KCl, pH 6.2), the cells were fixed in 1 ml of ice-cold methanol for 5 min. The fixed cells were washed three times with standard PBST (phosphate-buffered saline containing 0.1% Tween 20) and blocked with 5% non-fat dry milk in PBST at 4° C. overnight. Cells were then incubated with anti-APN IgG (1 µg/ml) in PBST containing 0.1% dry milk at room temperature for 1 h. After incubation cells were washed three times, then incubated With Alexa-conjugated goat anti-rabbit IgG (Molecular Probes, Eugene, Oreg.) (1:1000) in PBST containing 0.1% dry milk for 1 hour at room temperature. Immunostained cells were observed using fluorescence microscopy or fluorescence confocal microscopy (Center for Advanced Ultrastructural Research, University of Georgia).

3.4 Assays of aminopeptidase N Activity

Sf21 cells transfected with pHSP120 or pHSP-HR5 were collected and washed two times with PBS. The cells were suspended in 2 ml PBS and then homogenized with Potter-Helvehjem homogenizer. The cell homogenate was centrifuged at 27,000×g for 15 min at 4° C. The pellet was re-suspended in 2 ml of 10 mM Tris-HCl, 150 mM NaCl, pH 7.4. APN activity was assayed with L-leucine-p-nitroanilide as substrate as described previously (4). Briefly, the APN substrate (50 μl 6.8 mg/ml in methanol) was mixed with 1.4 ml of substrate buffer (10 mM Tris-HCl, 150 mM NaCl pH 7.4), and then the homogenate (50 μg of proteins) was added. The sample solution was incubated at 37° C. for 2 h. The level of APN activity was then determined by spectrophotometric measurement of free p-nitroanilide at 405 nM.

Results

*M. sexta* 120 kDa APN is attached to the epithelial membrane of midgut cells by a GPI anchor (Garczynski and Adang, 1995; Lu and Adang, 1996). Both 120 kDa APN1a and *M. sexta* APN1 have a putative GPI signal sequence at the C-terminus (FIG. 3; Knight et al., 1995 (SEQ ID NO: 11)). We examined the GPI-anchor properties of the expressed 120 kDa APN1a in Sf21 cells using anti-CRD antibody that is specific for the modified inositol product resulting from PIPLC cleavage. As shown in FIGS. 7A and B, expressed APN1a reacted with the anti-CRD antibody after PIPLC treatment (FIG. 7A, lane 2). Without PIPLC treatment, the anti-CRD antibody did not recognize expressed APN1a (FIG. 7B, lane 2). These results indicate that the expressed APN1a has an intact GPI anchor. Also, the anti-CRD antibody clearly recognized 115 kDa and 120 kDa protein bands (FIG. 7A, lane 2). These two processed forms of 120 kDa APN1a are likely due to differences in glycosylation. FIGS. 7A and B also revealed that the anti-CRD antibody did not bind to PIPLC-treated proteins in Sf21 cells not expressing APN1a (FIG. 7A, lane 1), thus indicating that Sf21 cells appear not to express any endogenous GPI-linked proteins. (FIG. 7A, lane 1), thus indicating that Sf21 cells appear not to express any endogenous GPI-linked proteins.

Figures 8A, 8B:
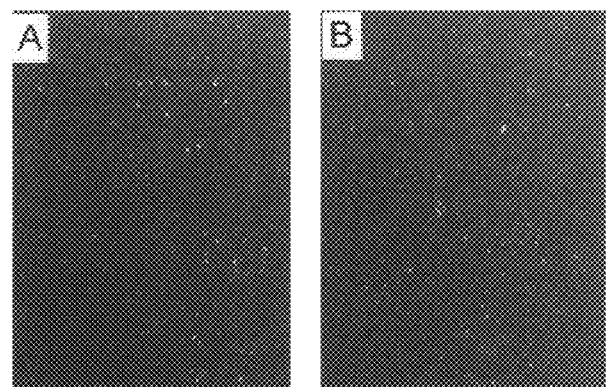
Figures 8C, 8D:
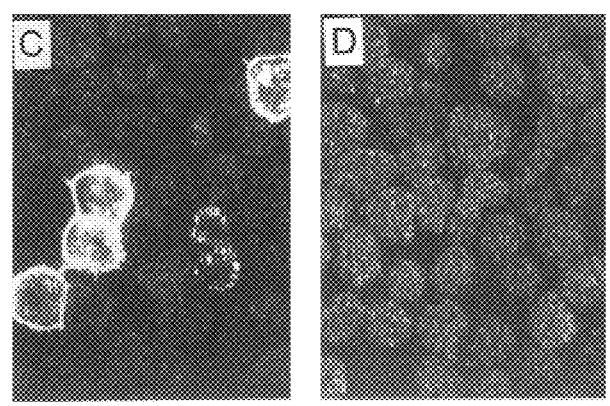

Since 120 kDa APN1a was expressed by transfected Sf11 cells as a GPI-linked protein, we investigated if APN1a was on the cell membrane surface by immunofluorescence microscopy. Sf21 cells on glass coverslips were incubated with anti-APN antibody and Alexa488-anti-IgG conjugate. Cells were viewed by fluorescence confocal microscopy. The results are shown in FIGS. 8A–8D. An intense fluorescent signal specific for anti-APN antibody was observed on some Sf21 cells (FIG. 8C), indicating that expressed APN1a was located primarily on the extracellular membrane. Sf21 cells transfected with control vector, pHSP-HR5, showed no significant immunofluorescence (FIG. 8D). Also, Sf21 cells stained with pre-immune serum did not show any fluorescent signal (FIG. 8A and 8B).

APN Activity Assays of the Expressed *M sexta* APN1a

Sf21 cells transfected with pHSP120 or pHSP-HR5 were collected and homogenized. The homogenate (50 μg of proteins) was tested for APN activity. The results were shown in FIG. 9. A high level of APN activity was present in the cells transfected pHSP120 compared with that in the cells transfected with pHSP-HR5 (FIG. 9, columns A and C). Amastatin, an APN inhibitor, greatly reduced APN activity of pHSP120-transfected Sf21 cells (FIG. 9, column B). In contrast, amastatin did not show significantly impact on enzymatic activity of Sf21 cells transfected with pHSP-HR5 (FIG. 9, column D).

EXAMPLE 4

4.1 Purification and Labeling of *B. thuringiensis* Toxins

Growth of *B. thuringiensis* strains, trypsin activation, and fast-performance liquid chromatography (Pharmacia) purification of Cry1Ac, Cry1Ca and Cry3a toxins were done as previously described (Garczynski et al 1991; Lu and Adang 1996). Two forms (55 kDa and 65 kDa) of Cry1Ba toxins were kindly provided by Dr. Masson (Biotechnology Research Institute, National Research Council of Canada, Canada). The purified Cry1Ac and Cry1Ba (200 $\mu$g) were labeled with 5-(and-6)-carboxytetramethylrhodamine, succinimidyl ester [5(6)-TAMRA SE] (Molecular Probe, Eugene, Oreg.) according to the manufacturer's instructions. Briefly, 5(6)-TAMRA (5 mg) were dissolved in 0.5 ml of Dimethylformamide (DMF) immediately before starting the labeling. The dye solution (100 $\mu$l) was slowly added into 500 $\mu$l of toxin sample (200 $\mu$g toxins) and incubated for 1 h at room temperature. The reaction was stopped by adding 0.1 ml of 1.5 M hydroxylamine, pH 8.5, and then the mixture was incubated. for 1h at room temperature. The sample was applied onto a 25 ml of G-50 gel filtration column (1.5×25 cm) equilibrated with 20 mM $Na_2CO_3$, pH 9.6. The fractions containing toxins were pooled and stored at −80° C. until use.

4.2 Binding of *B. thuringiensis* Toxins and Anti-APN Serum to Sf21 Cells

Sf21 cells were plated onto a microscope cover glass (18×18 mm) in a tissue culture dish (60×15 mm diameter), and then transfected and heat-shocked as described above. After three washes with Insect PBS (1 mM $Na_2HPO_4$, 10.5 mM $KH_2PO_4$, 140 mM NaCl, 40 mM KCl, pH 6.2), the cells were fixed in 1 ml of ice-cold methanol for 5 min. The fixed cells were washed three times with standard PBST (phosphate-buffered saline containing 0.1% Tween 20) and blocked with 5% non-fat dry milk in PBST at 4° C. overnight. Cells were then incubated with either rhodamine-labeled *B. thuringiensis* toxins (1 $\mu$g /ml) or anti-APN IgG (1 $\mu$g/ml) in PBST containing 0.1% dry milk at room temperature for 1 h. The incubation cells were washed three times with PBST. And then the cells treated by anti-APN antibody were further incubated with Alexa488-conjugated goat anti-rabbit IgG (Molecular Probes, Eugene, Oreg.) (1:1000) in PBST containing 0.1% dry milk for 1 hour at room temperature. Immunostained cells were observed using fluorescence microscopy or fluorescence confocal microscopy (Center for Advanced Ultrastructural Research, University of Georgia).

4.3 Affinity Purification and Immunoblot Analyses of 120 kDa APN

Affinity purification method of *M. sexta* 120 kDa APN from Sf21 cells or *M. sexta* midgut BBMV was described in Luo et al (1996). Briefly, Cry1Ac, Cry1Ba and Cry3a toxins (200 μg) were coupled to 400 μl of cyanogen bromide-activated Sepharose 4B in 20 mM Na$_2$CO$_3$, pH 9.6. *M sexta* BBMV (1 ml, 3.4 mg/ml proteins) or Sf21 cells (10$^7$ cells) were solubilized with 2% 3-[(3-cholamidopropyl)dimethylammoniol]-1-propane-sulphonate (CHAPS) in buffer A (50 mM Na$_2$CO$_3$, pH 9.6, 200 mM NaCl, 5 mM EGTA, 0.1% CHAPS). Insoluble material was removed by centrifugation at 27,000×g for 30 min at 4° C. CHAPS-solubilized BBMV (1 ml) or Sf21 cells (2 ml) were then added to the toxin-coupled Sepharose beads equilibrated with Buffer A. The mixture was incubated at 4° C. overnight. After washing with 100 ml of Buffer A, the binding protein-toxin complex was dissociated from the beads by heating in SDS-PAGE sample buffer at 100° C. for 5 min. The samples were separated by 8% SDS-PAGE, and then electrophoretically transferred to nitrocellulose membrane (Millipore Corp., Bedford, Mass.) in transfer buffer (Towbin et al., 1979) at 4° C. overnight. The membrane was blocked with 5% non-fat dry milk in PBST at room temperature for 1 h, and then probed with anti-APN antibody (0.5 μg/ml) in PBST containing 0.1% non-fat dry milk for 2 h. After three washes with PBST, the membrane was incubated with horseradish peroxidase (HRP)-conjugated donkey anti-rabbit IgG (1:3000) (Amersham, Piscataway, N.J.) in PBST containing 0.1% non-fat dry milk at room temperature for 2 h. Protein bands were visualized with ECL Western Blotting Kit (Amersham, Piscataway, N.J.) according to manufacturer's instructions.

4.4 Toxicity Assays

Sf21 cells (1.8×10$^6$) were grown and heat-shocked as described above. Cry1Ac, Cry1Ba and Cry1Ca toxins were diluted to 5,10,25, and 40 μg/ml with insect PBS, pH 6.2. The freshly prepared toxin solution (1 ml) was added to each Sf21 cell plate and incubated at room temperature for 2 h. Cell mortality was determined by trypan blue staining as described by Thomas and Ellar (1983).

Results

Previous studies showed that *M. sexta* 120 kDa APN bound specifically to Cry1Aa, Cry1Ab and Cry1Ac, but not Cry1C or Cry1E toxins (Knight et al., 1994; Sangadala et al., 1994; Masson et al., 1995; Lu and Adang, 1996). Since the expressed 120 kDa APN located on Sf21 cell surfaces, we examined the binding of Cry1toxins to Sf21 cells using double immunofluorescence staining. Sf21 cells on glass coverslips were incubated with anti-APN antibody and rhodamine-labeled toxins. And then cells were viewed by fluorescence confocal microscopy. The results were shown in FIGS. 10A–D, 11A–D, and 12A–D. No fluorescence was detected in Cry1Ac-staining Sf21 cells (FIGS. 10B and D), suggesting that Cry1Ac does not bind to the expressed APN. The 55 kDa form of Cry1Ba toxin bound strongly to Sf21 cells transfected with pHSP120 (FIG. 11D), but not to Sf21 cells transfected with pHSP-HR5 (FIG. 10B). However, the 65 kDa form of Cry1Ba only bound weakly to some Sf21 cells transfected with pHSP120 (FIGS. 12B–D).

*B. thuringiensis* toxin affinity chromatography was used to purify the expressed *M. sexta* APN from Sf21 cells. CHAPS-solubilized Sf21 cells were applied to Cry1Ac, Cry1Ba or Cry3a affinity column, respectively. The bound proteins were dissociated from the column, and separated by SDS-PAGE. The proteins were electrophoretically transferred to nitrocellulose membrane and then probed with anti-APN antibody. The results were shown in FIG. 13. The 55 kDa form of Cry1Ba bound strongly to the expressed 120 kDa APN from Sf21 cells (FIG. 13, lane 1) and native 120 kDa APN from *M sexta* BBMV (FIG. 13, lane 5). In contrast, the 65 kDa form of Cry1Ba bound weakly to 120 kDa APN from both Sf21 cells and *M sexta* BBMV (FIG. 13, lanes 2 and 6). Cry1Ac and Cry3a toxins did not bind to the expressed 120 kDa APN from Sf21 cells (FIG. 13, lanes 3 and 4).

The toxicity of three Cry1toxins to Sf21 cells expressing *M sexta* 120 APN was determined. A single concentration of Cry1toxins (40 μg/ml) was used and the cell mortality was measured by Trypan blue staining (Thomas and Ellar 1983). The results were shown in Table 1. As reported previously (Wang and McCarthy 1997), Cry1Ca is highly toxic to Sf21 cells, since more than 85% of the cells were killed 2 h after incubation with Cry1Ca toxin (Table 1). Cry1Ac showed low toxicity to both Sf21 cells transfected with pHSP120 and control plasmid pHSP-HR5, and no significant difference between two treatments was observed (Table 1). The 65 kDa form of Cry1Ba had low toxicity to Sf21 cells. The mortality of cells is about 17% (Table 1). Interestingly, it was found that the 55. kDa form of Cry1Ba is highly toxic to Sf21 cells that expressed *M sexta* 120 kDa APN (Table 1). The mortality of Sf21 cells transfected with pHSP120 is 47.3%, while the mortality of the cells transfected with control vector only is 30.0% (Table 1). The concentration dependence of Cry1Ba (55 kDa form) to Sf21 cells transfected with pHSP120 and pHSP-HR5 was further investigated. The results showed that for three toxin concentrations (10, 25, and 40 μg/ml, n=3) significant difference in mortality between the pHSP120-transfected Sf21 cells and pHSP-HR5-transfected cells was observed (FIG. 14). Taken together, these results demonstrate that the 120 kDa APN expressed in Sf21 cells increased the binding and toxicity of 55 kDa form of Cry1Ba to Sf21 cells.

TABLE 1

Toxicity of Three Cry1 Toxins to Sf21 cells

| | Mortality (%) (±SE)[a] | |
| --- | --- | --- |
| Toxin | Cells transfected with pHSP 120[b] | Cells transfected with pHSP-HR5[c] |
| Cry1Ba (55 kDa) | 47.3 (±3.2) | 30.0 (±2.3) |
| Cry1Ba (65 kDa) | 17.6 (±0.9) | 16.5 (±0.1) |
| Cry1Ac | 20.0 (±0.4) | 20.6 (±0.5) |
| CryaCa | 85.7 (±1.1) | 84.9 (±0.5) |

[a]Cell mortality was determined by Trypan blue (0.1%) staining 2 h after incubation with 40 μg/ml of Cry1Ba, Cry1Ac, and Cry1Ca toxins in insect PBS.
Results are means of three assays (±standard error)
[b]Plasmid pHSP120 contains a full-length *M. sexta* 120 kDa APN cDNA.
[c]Plasmid pHSP-HR5 is a control vector without *M. sexta* APN cDNA.

EXAMPLE 5

5.1 Construction of the Expression Vector pHSP120

The plasmid pHSP70PL that contains the *Drosophila melanogaster* HSP70 promoter and the 5' untranslated leader of HSP70 is described by Morris and Miller (1992). We first constructed plasmid pHSP-HR5. This plasmid contains the polyadenylation sequence (poly A) from the p35 gene and half of the homologous region 5 (hr5) of *Autographa californica* nuclear polyhedrosis virus (AcMNPV), a sequence extending from nucleotide 17,344 to 17,636. Two PCR primers (5'-pAHR5: 5'GGAAGATCT-TCCACTGCATGCGTAACTAGTGCACTCAAC3' (SEQ ID NO: 14) and 3'-pAHR5: 5'GGGATCCCGTC-CCCGCGGGGACTCGATTTGAAAAA-CAAATGACCATCATC 3' (SEQ ID NO: 15)) were designed to amplify the polyA and a part of the hr5 sequence from the plasmid pH1PQ which contains the Hind III Q restriction fragment of AcMNPV genomic DNA. The PCR product (316 bp) was digested with BgIII and BamHI, and then inserted into pHSP70PL vector treated with BgIII. The resulting plasmid called pHSP-HR5. Plasmid pHSP120 was then constructed by inserting a 3.2 kb SphI/BamHI fragment of pAPN 120 into pHSP-HR5. All plasmids were verified by restriction enzyme analyses and DNA sequencing.

5.2 Construction of pHSPAC120

Plasmid pBSIE1Gpac, which contains Puromycin acetyl-transferase (Pac) gene under IE1 promoter control, was digested with EcoRV and BamHI. A 1.6 kb fragment contained Pac gene and IE1 promoter was purified, and then inserted into pHSP120 treated with the same enzymes. The resulting vector, called pHSPAC120, was verified by restriction enzyme digestion.

5.3 Selection of Stable Sf21 Cell Line

The pHSPAC120 plasmid DNA was isolated and purified using a Plasmid Maxi Kit (Qiagen, Valencia, Calif.). Sf21 cells were plated at $1.8 \times 10^6$ cells per plate (60 mm diameter) prior to transfection with pHSPAC120 DNA. Plasmid DNA (10 μg) was mixed with 5 μl of Lipofectin reagent and combined with 1 ml of TC-100 medium. The mixture was incubated at room temperature for 15 min. Following 3 washes with TC-100 medium, the DNA/Lipofectin mixture was added to the cells, and then the cells were incubated at room temperature for 4 h on a rocker. After removal of DNA/Lipofectin mixture, TC-100 with 10% fetal bovine serum (4 ml) was added to the plates and the cells were incubated at 27° C. overnight. After the medium was removed, the fresh medium (4 ml) containing different concentrations of puromycin (1 μg, 2 μg and 4 μg/ml) was added to different plates respectively. The cells were further incubated at 27° C. for three days. After removal of TC-100 media containing puromycin, 4 ml fresh media were added. The cells were cultured overnight. The alive cells were collected, and the resuspended in TC-100 containing 4 μg/ml puromycin. The cells were plated into a 60 mm plate and incubated for 3 days. The cells were then selected two more times using puromycin as described above.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Ayres, M.D., Howard, S. C., Kuzio, J., Lopez-Ferber, M. and Dossec, R. D. (1994) "The complete DNA sequence of *Autograph californica* nuclear polyhedrosis virus," *Virology* 202:586–605.

Benbacer, L., Kut, E., Besnardeau, L., Laude, H. and Delmas, B. (1997) "Interspecies aminopeptidase-N chimeras reveal species-specific receptor recognition by canine coronavirus, feline infectious peritonitis virus, and transmissible gastroenteritis virus," *J. Virol.* 71:734–737.

Chaudhri, M., Steverding, D., Kittelberger, D., Tjia, S. and Overath, P. (1994) "Expression of glycosylphosphadylinositol-anchored *Trypanosoma brucei* transferrin-binding protein complex in insect cells," *Proc. Natl. Acad. Sci. USA*. 91:6443–6447.

Davies, A. and Morgan, B. P. (1993) "Expression of the glycosylphosphatidlinositol-linked complement-inhibiting protein CD59 antigen in insect cells using a baculovirus vector," *Biochemical Journal* 295:889–896.

Delmas, B., Gelfi, J., Haridon, R. L., Vogel, L. K., Sjostrom, H., Noren, O. and Laude, H. (1992) "Aminopeptidase N is a major receptor for the enteropathogenic coronavirus TGEV," *Nature* 357:417–419.

Denolf, P., Hendrickx, K., Van Damme, J., Jansens, S., Peferoen, M., Degheele, D. and Van Rie, J. (1997) "Cloning and characterization of *Manduca sexta* and *Plutella xylostella* midgut aminopeptidase N enzymes related to *Bacillus thuringiensis* toxin-binding proteins," *Eur. J. Biochem.* 248:748–761.

Ferre, J., Real, M. D., Van Rie, J., Jansens, S. and Peferoen, M. (1991) "Resistance to the Bacillus thuringiensis bioinsecticide in a field population of Plutella xylostella is due to a change in a midgut membrane receptor," *Proc. Natl. Acad. Sci. USA* 88:5119–5123.

Fujii, H., Nakajima, M:, Saiki, I., Yoneda, J., Azuma, I., and Tsuruo, T. (1995) "Human-melanoma invasion and metastasis enhancement by high expression of aminopeptidase N/CD13," *Clin. Exp. Metast.* 13:337–344.

Garczynski, S. F. and Adang, M. J. (1995) "*Bacillus thuringiensis* CryIA(c) d-endotoxin binding aminopeptidase in the *Manduca sexta* midgut has a glycosyl-phosphatidylinositol anchor," *Insect Biochem. Mol. Biol.* 25:409–415.

Garczynski, S. F., Crim; J. W. and Adang. M. J. (1991) "Identification of putative brush border membrane binding proteins specific to *Bacillus thuringiensis* delta-endotoxin by protein blot analysis," *Appl. Environ. Microbiol.* 57:2816–2820.

Gill, S., Cowles, E. A. and Francis, V. (1995) "Identification, isolation, and cloning of a *Bacillus thuringiensis* Cry1Ac toxin-binding protein from the midgut of the lepidopteran insect Heliothis virescens," *J. Biol. Chem.* 270:27277–27282. Hua, G., Tsukamoto, K., Rasilo, M. and Ikezawa, H. (1998) "Molecular cloning of a GPI-anchored aminopeptidase N from *Bombyx mori* midgut: a putative receptor for *Bacillus thuringiensis* Cry1A toxin," *Gene* 214:177–185.

Kennard, M. L., Shimizu, K. Y., Gabathuler, R., Rothenberger, S., Therlmann, D. and Jefferies, W. A. (1997) "Expression of cell surface GPI-anchored human p97 in baculovirus-infected insect cells," *Biotech. Bioeng.* 55:41–53.

Kenny, A. J., Stephenson, S. L. and Turner, A. J. (1987) "Cell surface peptidases," In Kenny, A. J. and Turner, A. J. (eds.) *Mammalian ectoenzymes*, Elsevier, Amsterdam, pp. 169–210.

Knight, P. J. K., Crickmore, N. and Ellar, D. J. (1994) "The receptor for *Bacillus thuringiensis* CryIA(c) delta-endotoxin in the brush border membrane is aminopeptidase N," *Mol. Microbiol.* 11:429–436.

Knight, P. J. K., Knowles, B. H. and Ellar, D. J. (1995) "Molecular cloning of an insect aminopeptidase N that serves as a receptor for *Bacillus thuringiensis* CryIA(c) toxin," *J. Biol. Chem.* 270:17765–17770.

Kolb, A. F., Maile, J., Heister, A. and Siddell, S. G. (1996) "Characterization of functional domains in the human coronavirus HCV 229E receptor," *J. Gen. Viro.* 77:2515–2521.

Kozak, M. (1987) "An analysis of 5'-noncoding sequences from 699 vertebrate messenger RNAs," *Nucl. Acids Res.* 15:8125–8132.

Laemmli, U. K. (1970) "Cleavage of structural proteins during the assembly of the head of bacteriophage T4," *Nature* 227:680–685.

Look, A. T., Ashmun, R. A., Shapiro, L. H. and Peiper, S. C. (1989) "Human myeloid plasma membrane glycoprotein CD13 (gp 150) is identical to aminopeptidase N," *J. Clin. Invest.* 83:1299–1307.

Lu, Y. and Adang, M. J. (1996) "Conversion of *Bacillus thuringiensis* CryIAc-binding aminopeptidase to a soluble form by endogenous phosphatidylinositol phospholipase C," *Insect Biochem. Molec. Biol.* 226:33–40.

Luo, K., Lu, Y. J. and Adang, M. J. (1996) "A 106 kDa form of aminopeptidase is a receptor for *Bacillus thuringiensis* CryIC delta-endotoxin in the brush border membrane of *Manduca sexta*," *Insect Biochem. Mol. Biol.* 26:783–791.

Luo, K., Sangadala, S., Masson, L., Mazza, A., Brousseau, R. and Adang, M. J. (1997a) "The *Heliothis virescens* 170-kDa aminopeptidase functions as 'Receptor A' by mediating specific *Bacillus thuringiensis* Cry1A d-endotoxin binding and pore formation," *Insect Biochem. Mol. Biol.*

Luo, K., Tabashnik, B. E. and Adang, M. J. (1997b) "Binding of *Bacillus thuringiensis* Cry1Ac toxin to aminopeptidase in susceptible and resistant diamondback moths (*Plutella xylostella*)," *Appl. Environ. Microbiol.* 63:1024–1027.

Luo, K., McLachlin, J. R., Brown, M. R., Adang, M. J. (1999) "Expression of a Glycosylphosphatidylinositol-Linked *Manduca sexta* Aminopeptiase N in Insect Cells," *Protein Expression and Purification* 17:113–122.

Masson, L., Lu, Y., Mazza, A., Brosseau, R. and Adang, M. J. (1995) "The CryIA(c) receptor purified from *Manduca sexta* displays multiple specificities," *J. Biol. Chem.* 270:20309–20315.

McConville, M. J. and Ferguson, M. A. J. (1993) "The structure, biosynthesis and function of glycosylated phosphatidylinositols in the parasitic protozoa and higher eukaryotes," *Biochemical Journal* 294:305–324.

McLaughlin, S. and Aderem, A. (1995) "The myristoyl-electrostatic switch: a modulator of reversible protein-membrane interactions," *TIBS* 20:272–276.

Morris, T. D. and Miller, L. K. (1992) "Promoter influence on baculovirus-mediated gene expression in permissive and non-permissive insect cell lines," *J. Virol.* 66:7397–7405.

Plakidou-dymock, S., Tanner, M. J. and McGivan, J. D. (1993) "A role for aminopeptidase N in Na⁺-dependent amino acid transport in bovine renal brush-border membranes," *Biochem. J.* 290:59–65.

Richardson, M. A., Smith, D. R. J., Kemp, D. H. and Tellam, R. L. (1993) "Native and baculovirus-expressed forms of the immunoprotective protein BM86 from *boophilus microplus* are anchored to the cell membrane by a glycosylphosphatidyl inositol linkage," *Insect Mol. Biol.* 1:139–147.

Sambrook et al. (1989) Molecular Cloning: A Laboratory Manual Cold Spring Harbor Laboratory Press, Cold Spring Harbor, N.Y.

Sangadala, S., Walters, F., English, L. H. and Adang, M. J. (1994) "A mixture of *Manduca sexta* aminopeptidase and alkaline phosphatase enhances *Bacillus thuringiensis* insecticidal CryIA(c) toxin binding and $^{86}Rb^{+}$-$K^{+}$ leakage in Vitro," *J. Biol. Chem.* 269:10088–10092.

Schwartz, J.-L., Lu, Y. J., Soehnlein, P., Brousseau, R., Masson, L., Laprade, R. and Adang, M. J. (1997) "Ion channels formed in planar lipid bilayers by *Bacillus thuringiensis* toxins in the presence of *Manduca sexta* midgut receptors," *FEBS Lett.* 412:270–276.

Takasaki, S., Erickson, R. H., Kim, Y. S., Kochibe, N. and Kobata, A. (1991) "N-linked neutral sugar chains of aminopeptidase N purified from rat small intestinal brush-border membrane," *Biochem.* 30:9102–9110.

Tomita, M., Obara, H., Takesue, Y., Tamura, H.-O., Miyajima, s., Taguchi, R. and Ikezawa, H. (1 994) "Purification of glycosylphosphatidylinositol-anchoring aminopeptidase N from the plasma membrane of larval midgut epithelial cells of the silkworm, *Bombyx mori*," *Int. J. Biochem.* 26:977–986.

Towbin, H., Staehelin, T. and Gordon, J. (1979) "Electrophoretic transfer of proteins from polyacrylamide gels to nitrocellulose sheets: procedure and some applications," *Proc. Natl. Acad. Sci. USA* 76:4350–4354.

Tresnan, N. B., Levis, R. and Holmes, K. V. (1996) "Feline aminopeptidase N serve as a receptor for feline, canine, porcine, and human coronaviruses in serogroup I," *J. virol.* 70:8669–8674.

Valaitis, A., Lee, M. K., Rajamohan, F. and Dean, D. H. (1995) "Brush border membrane aminopeptidase-N in the midgut of the gypsy moth serves as the receptor for the CryIA(c) d-endotoxin of *Bacillus thuringiensis*," *Insect Biochem. Molec. Biol.* 25:1143–1151.

Vaughn, J. L., Goodwin, R. H., Tompkins, G. L. and McCawley, P. (1977) "The establishment of two insect cell lines from the insect *Spodoptera frugiperda* (Lepidoptera:Noctuidae)," *In Vitro Cell. Dev. Biol.* 13:213–217.

Wolfersberger, M. G., Luthy, P., Maurer, A., Parenti, P., Sacchi, V. F., Giordana, B. and Hanozet, G.M. (1987) "Preparation and partial characterization of amino acid transporting brush border membrane vesicles from the larval midgut of the cabbage butterfly (*Pieris brassicae*)," *Comp. Biochem. Physiol.* 86A:301–308.

Yaoi, K., Kadotani, T., Kuwana, Shinkawa, A., Takahashi, T., Iwahana, H. and Sato, M. (1997) "Aminopeptidase N from *Bombyx mori* as a candidate for the receptor of *Bacillus thuringiensis* Cry1Aa toxin," *Eur. J. Biochem.* 246:652–657.

Yeager, C. L., Ashmun, R. A., Williams, R. K., Cardellichio, C. B., Shapiro, L. H., Look, A. T. and Holmes, K. V. (1992) "Human aminopeptidase N is a receptor for human coronavirus 229E," *Nature* 357:420–422.

We claim:

1. An isolated polynucleotide comprising the sequence depicted in SEQ ID NO: 2, or a fragment thereof sufficient to encode a functional protein.

2. A polynucleotide according to claim 1, wherein said polynucleotide comprises SEQ ID NO: 2.

3. A polynucleotide according to claim 1, wherein said polynucleotide is expression vector pHSP120.

4. A transgenic cell comprising a heterologous polyaucleotide encoding an aminopeptidase N (APN), wherein said polynucleotide comprises the sequence depicted in SEQ ID NO: 2 or a fragment thereof sufficient to encode a fictional protein.

5. A transgenic cell according to claim 4, wherein said polynucleotide comprises SEQ ID NO: 2.

6. A method of identifying a cytotoxic agent wherein said method comprises the steps of obtaining a transgenic cell comprising a heterologous polynucleotide encoding an APN, wherein said polynucleotide comprises the sequence depicted in SEQ ID NO: 2 or a fragment thereof sufficient to encode a functional protein; and using said cell to screen at least one compound for its ability to produce a cytotoxic effect on said cell, whereby a cytotoxic agent is identified.

7. A method according to claim 6, wherein said polynucleotide comprises SEQ ID NO: 2.

8. A method of screening for aminopeptidase inhibitors wherein said method comprises the steps of:

a) obtaining a plurality of transgenic cells comprising a heterologous polynucleotide encoding an APN, wherein said polynucleotide comprises the sequence depicted in SEQ D NO: 2 or a fragment thereof sufficient to encode a functional protein;

b) exposing said cells to at least one compound of interest; and c) monitoring said exposed cells for an inhibitive effect attributable to said exposure step.

9. A method according to claim 8, wherein said polynucleotide comprises SEQ ID NO: 2.

* * * * *

UNITED STATES PATENT AND TRADEMARK OFFICE
CERTIFICATE OF CORRECTION

PATENT NO. : 6,586,197 B1
DATED : July 1, 2003
INVENTOR(S) : Michael J. Adang and Ke Luo It is certified that error appears in the above-identified patent and that said Letters Patent is hereby corrected as shown below:

Column 2,
Line 3, "et a," should read -- *et al.*, --.
Line 11, "et al" should read -- *et al.* --.
Line 29, "fill length" should read -- full length --.

Column 3,
Line 14, "Sf21" should read -- Sf21 cells. --.
Line 16, "antiserium." should read -- antiserum. --.
Line 27, "toxin 55 kDa form)" should read -- toxin (55 kDa form) --.

Column 5,
Line 17, "linked. to" should read -- linked to --.

Column 6,
Line 17, "SEQ ED NO: 2" should read -- SEQ ID NO: 2 --.
Lines 40-44, "listed herein without the expense of undue experimentation. sequence. Following the teachings herein and using knowledge and techniques well known in the art, the skilled worker will be able to make a large number of operative embodiments having equivalent DNA sequences to those listed herein without the expense of undue experimentation." should read -- listed herein without the expense of undue experimentation. --.
Line 51, "et al" should read -- *et al.* --.

Column 8,
Line 32, "IEI promoter" should read -- IE1 promoter --.

Column 9,
Line 13, "cells. May" should read -- cells may --.

Column 10,
Line 63, "Bg11I" should read -- Bg1II --.

Column 11,
Line 10, "EcoRV-XhoI" should read -- EcoRV-XhoI --.

UNITED STATES PATENT AND TRADEMARK OFFICE
CERTIFICATE OF CORRECTION

PATENT NO. : 6,586,197 B1
DATED : July 1, 2003
INVENTOR(S) : Michael J. Adang and Ke Luo It is certified that error appears in the above-identified patent and that said Letters Patent is hereby corrected as shown below:

Column 13,
Line 2, "BglII" should read -- BglII --.
Lines 3-14, "enzyme analyses and DNA sequencing.   5' GGGATCCCGTCCCCGC GGGGACTCGATTTGAAAAACAAATGACCATCATC3' (SEQ ID NO: 9)) were designed to amplify the poly A and a part of the hr5 sequence from the plasmid pH1PQ which contains the Hind III Q restriction fragment of AcM-NPV genomic DNA. The PCR product (316 bp) was digested with BglII and BamHI, and then inserted into pHSP70PL vector treated with BglII. The resulting plasmid, pHSP-HR5, was verified by restriction enzyme analyses and DNA sequencing." should read -- enzyme analyses and DNA sequencing. --.
Line 20, "S21 Cells" should read -- Sf21 Cells --.

Column 15,
Lines 46-48, "Sf21 cells appear not to express any endogenous GPI-linked proteins. (FIG. 7A, lane 1), thus indicating that Sf21 cells appear not to express any endogenous GPI-linked proteins." should read -- Sf21 cells appear not to express any endogenous GPI-linked proteins. --.
Line 49, "Sf11" should read -- Sf21 --.

Column 16,
Line 32, "incubated. for" should read -- incubated for --.

Column 17,
Line 5, "dimethylammoniol]-1" should read -- dimethylammonio]-1 --.

Column 18,
Line 21, "55. kDa" should read -- 55 kDa --.

UNITED STATES PATENT AND TRADEMARK OFFICE
CERTIFICATE OF CORRECTION

PATENT NO. : 6,586,197 B1
DATED : July 1, 2003
INVENTOR(S) : Michael J. Adang and Ke Luo It is certified that error appears in the above-identified patent and that said Letters Patent is hereby corrected as shown below:

<u>Column 57,</u>
Lines 18-19, "polyaucleotide" should read -- polynucleotide --.
Line 21, "fictional protein" should read -- functional protein --.

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,586,197 B1
DATED : July 1, 2003
INVENTOR(S) : Michael J. Adang and Ke Luo It is certified that error appears in the above-identified patent and that said Letters Patent is hereby corrected as shown below:

Column 2,
Line 6, "This application claims benefit of U.S. Provisional Application Ser. No. 60/153,116, filed Sep. 7, 1999." should read -- This application claims the benefit of U.S. Provisional Application Ser. No. 60/153,116, filed Sep. 7, 1999.

GOVERNMENT INTEREST STATEMENT

This invention was made in part with government support under Grant No. NIH AI29092 awarded by the National Institutes of Health and under Grant Nos. USDA/NRI 95-37302-1803 and 95-37302-4548 awarded by the U.S. Department of Agriculture/National Research Initiative. The government may have certain rights in this invention. --.

Signed and Sealed this

Third Day of August, 2004

JON W. DUDAS
*Acting Director of the United States Patent and Trademark Office*